United States Patent
Sode et al.

(10) Patent No.: US 12,116,610 B2
(45) Date of Patent: Oct. 15, 2024

(54) GLYCEROL 3-PHOSPHATE OXIDASE MUTANTS, COMPOSITIONS, DEVICES, KITS AND USES THEREOF

(71) Applicant: The University of North Carolina at Chapel Hill, Chapel Hill, NC (US)

(72) Inventors: Koji Sode, Chapel Hill, NC (US); Junko Shimazaki, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 17/585,119

(22) Filed: Jan. 26, 2022

(65) Prior Publication Data

US 2022/0235391 A1    Jul. 28, 2022

Related U.S. Application Data

(60) Provisional application No. 63/141,740, filed on Jan. 26, 2021.

(51) Int. Cl.
| | |
|---|---|
| *C12N 9/04* | (2006.01) |
| *C12Q 1/00* | (2006.01) |
| *C12Q 1/26* | (2006.01) |

(52) U.S. Cl.
CPC .......... *C12Q 1/005* (2013.01); *C12N 9/0006* (2013.01); *C12Q 1/26* (2013.01); *C12Y 101/03021* (2013.01)

(58) Field of Classification Search
CPC ........ C12Q 1/005; C12Q 1/26; C12N 9/0006; C12Y 101/03021; G01N 33/92; G01N 2405/02

See application file for complete search history.

(56) References Cited

U.S. PATENT DOCUMENTS

| | | |
|---|---|---|
| 5,334,508 A | 8/1994 | Hoenes |
| 6,036,919 A | 3/2000 | Thym et al. |
| 7,008,799 B1 | 3/2006 | Zimmer et al. |

FOREIGN PATENT DOCUMENTS

CN    115247158    * 10/2022

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Guo et al., PNAS 101(25):9205-9210, 2004.*

* cited by examiner

*Primary Examiner* — Delia M Ramirez
(74) *Attorney, Agent, or Firm* — Alston & Bird LLP

(57) ABSTRACT

Compositions, devices, kits and methods are disclosed for assaying triglyceride with a glycerol 3-phosphate oxidase mutant. The glycerol 3-phosphate oxidase mutant has reduced oxidase activity while substantially maintaining, or increasing, its dehydrogenase activity, compared to the wild-type glycerol 3-phosphate oxidase.

15 Claims, 16 Drawing Sheets

Specification includes a Sequence Listing.

Figure 1

Triglyceride sensor 1

Triglyceride + H₂O  —*Lipoprotein lipase*→  Glycerol + Fatty acids

Glycerol + ATP  —*Glycerol Kinase*→  Glycerol-3-Phosphate + ADP

Glycerol-3-Phosphate + O₂  —*Glycerol 3-phosphate oxidase*→  Dihydroxyacetone phosphate + H₂O₂

H₂O₂ + Phenol + 4-AAP  —*Peroxidase*→  Quinoneimine dye + H₂O

*Mediator: Hexaammine ruthenium(III) chloride (CAS# 14282-91-8)

**Glp: D/L-glycerol-3-phosphate

*Glp: D/L-glycerol-3-phosphate

*Glp; D/L-glycerol-3-phophate

GLYCEROL 3-PHOSPHATE OXIDASE MUTANTS, COMPOSITIONS, DEVICES, KITS AND USES THEREOF

INCORPORATION OF SEQUENCE LISTING

An official copy of the Sequence Listing is submitted electronically via Patent Center as a Sequence Listing with a file named 573276_ST25.txt created on Jan. 14, 2022, having a size of 5593 bytes and is filed concurrently with the specification. The Sequence Listing contained in this document is part of the specification and is herein incorporated by reference in its entirety.

CROSS-REFERENCE TO RELATED APPLICATIONS

This application claims the benefit of and priority to U.S. Provisional Patent Application No. 63/141,740, filed on Jan. 26, 2021, the content of which is incorporated by reference herein in its entirety for all purposes.

BACKGROUND

Hypertriglyceridemia is a condition in which triglyceride levels are elevated, and is a common disorder in the United States. It is often caused or exacerbated by uncontrolled diabetes mellitus, obesity, and sedentary habits, all of which are prevalent in industrialized societies. Additionally, hypertriglyceridemia is a risk factor for coronary artery disease (CAD). Therefore, the concentration of triglycerides in blood is important in clinical tests and useful in diagnosing and controlling or preventing certain health conditions.

Elevated triglycerides are determined by direct laboratory analysis of serum or plasma after a 10- to 12-hour fast. The triglyceride concentration in blood can be measured using an enzyme having specificity to triglyceride such as, for example, glycerol 3-phosphate oxidase (EC 1.1.3.21; GlPOx). Currently, the enzyme, GlPOx is combined with lipase and glycerol kinase which catalyze the liberation of glycerol phosphate, the substrate of GlPOx. The GlPOx oxidizes glycerol phosphate, to liberate hydrogen peroxide to be colorimetrically measured with the combination of peroxidase colorimetric measurement.

Inherently, GlPOx uses oxygen as the primary electron acceptor. Therefore, the response of an electrochemical sensor with mediator using GlPOx is inherently affected by the oxygen. Additionally, there are issues with currently available glycerol dehydrogenases, such as the need to add NADH which is expensive for NADH-dependent dehydrogenases, and a lack of enzyme specificity.

There remains a need to develop a GlPOx whose activity is less affected by oxygen or oxygen concentration for improved sensitivity and accuracy in measuring triglycerides.

BRIEF SUMMARY

Compositions and methods are provided for assaying triglyceride in a sample from a subject.

In another aspect, provided herein are glycerol 3-phosphate oxidase mutants. In certain embodiments, provided herein are glycerol 3-phosphate oxidase mutants with a reduced oxidase activity as compared to the wild-type glycerol 3-phosphate oxidase, increased dehydrogenase activity compared to the wild-type glycerol 3-phosphate oxidase, or both.

In one aspect, provided herein is a glycerol 3-phosphate oxidase mutant comprising a sequence having at least 90% sequence identity to SEQ ID NO: 1, provided at least one of positions 99 to 109 or positions 164-174 is different from the amino acid occupying the corresponding position in SEQ ID NO: 1. In another aspect, provided herein is a glycerol 3-phosphate oxidase mutant comprising SEQ ID NO: 1 and provided at least one of position 104 or position 169 is different from the amino acid occupying the corresponding position in SEQ ID NO: 1.

In another aspect, provided herein are glycerol 3-phosphate oxidase mutants comprising a modification at one or more amino acid positions selected from a position corresponding to position 104 of the amino acid sequence set forth in SEQ ID NO: 1, a position corresponding to position 169 of the amino acid sequence set forth in SEQ ID NO: 1, or both.

In another aspect, provided herein are methods of assaying triglycerides in a sample, the method comprising the steps of: contacting the sample with the glycerol 3-phosphate oxidase mutant; and measuring an amount of the glycerol 3-phosphate oxidized by glycerol 3-phosphate oxidase mutant.

In another aspect, provided herein are devices for assaying triglyceride in a sample, the device comprising a glycerol 3-phosphate oxidase mutant and an electron mediator.

In another aspect, provided herein is a kit for assaying triglyceride in a sample, the kit comprising a glycerol 3-phosphate oxidase mutant and an electron mediator.

In another aspect, provided herein are enzyme electrodes comprising a glycerol 3-phosphate oxidase immobilized on an electrode. In another aspect, provided herein are enzyme sensors for assaying triglyceride comprising an enzyme electrode comprising a glycerol 3-phosphate oxidase mutant immobilized on an electrode as a working electrode.

BRIEF DESCRIPTION OF THE SEVERAL VIEWS OF THE DRAWING(S)

Having thus described the subject matter in general terms, reference will now be made to the accompanying drawings, which are not necessarily drawn to scale.

FIG. 1 illustrates the reaction in a triglyceride enzymatic analysis method and enzyme sensor that measures hydrogen peroxide.

Figure 2:
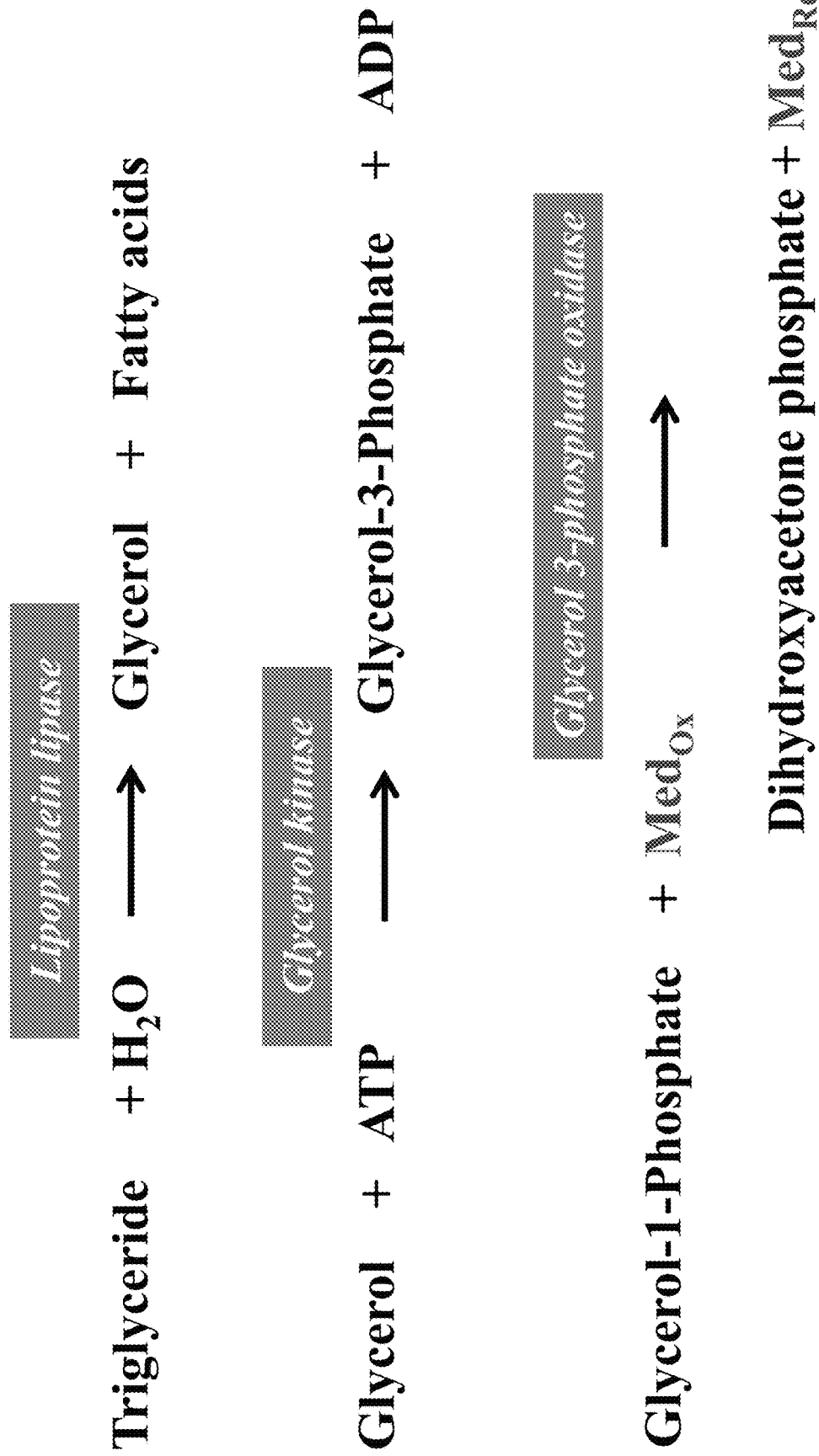
FIG. 2 illustrates the reaction in an electrochemical triglyceride sensor that utilizes an artificial electron acceptor or mediator instead of oxygen for the measurement.
Figure 3:
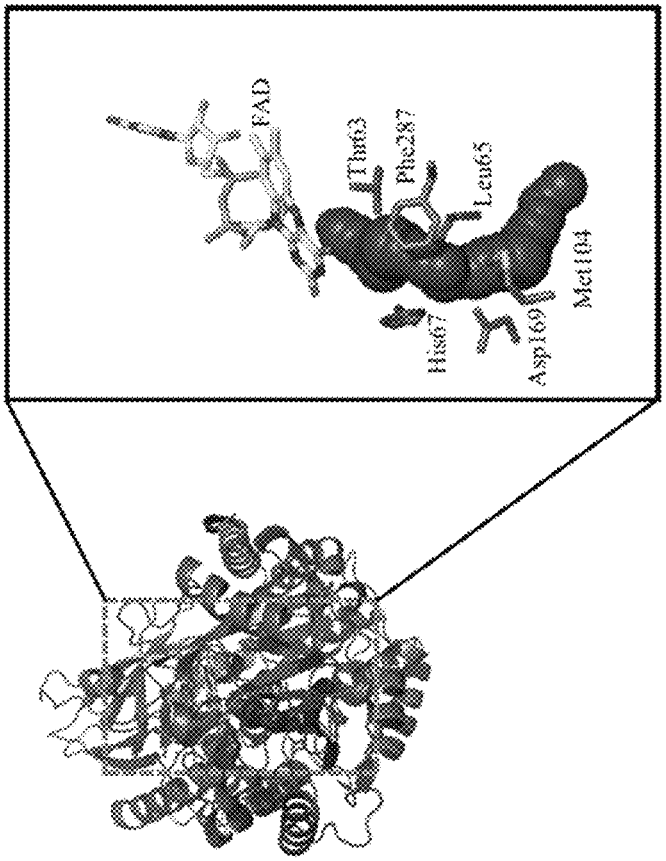
Figure 3:
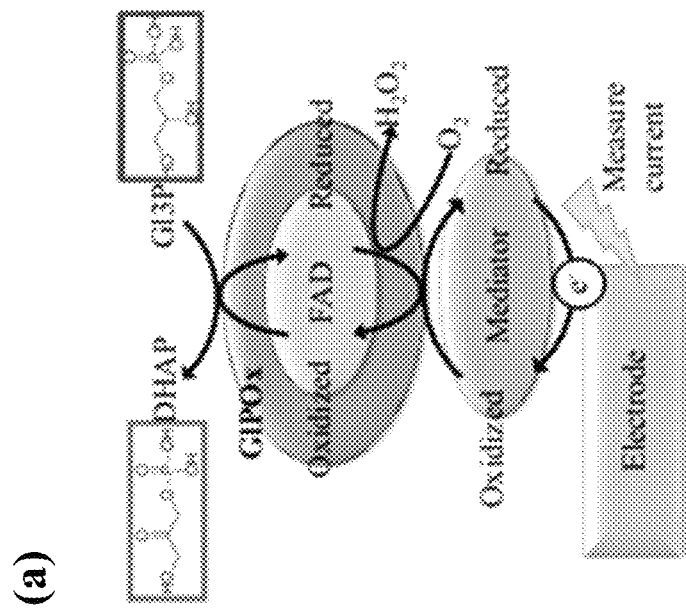

FIG. 3 illustrates (a) GlpOx uses $O_2$ as a natural electron carrier and (b) a model structure of AvGlpO and pathway predictions. The model structure of GlpO derived from *Aerococcus viridans* was constructed using *Streptococcus* GlpO (PDB:2RGH) as template. Positively charged residues are located at the entrance of the active site cavity. Therefore, charge bias around the pathway might affect the accessibility of the mediators with positively charged residues around predicted pathway. Positively charged mediators showed lower linearity compared to negatively charged mediators. Ferricyanide showed good linearity.

Figure 4:
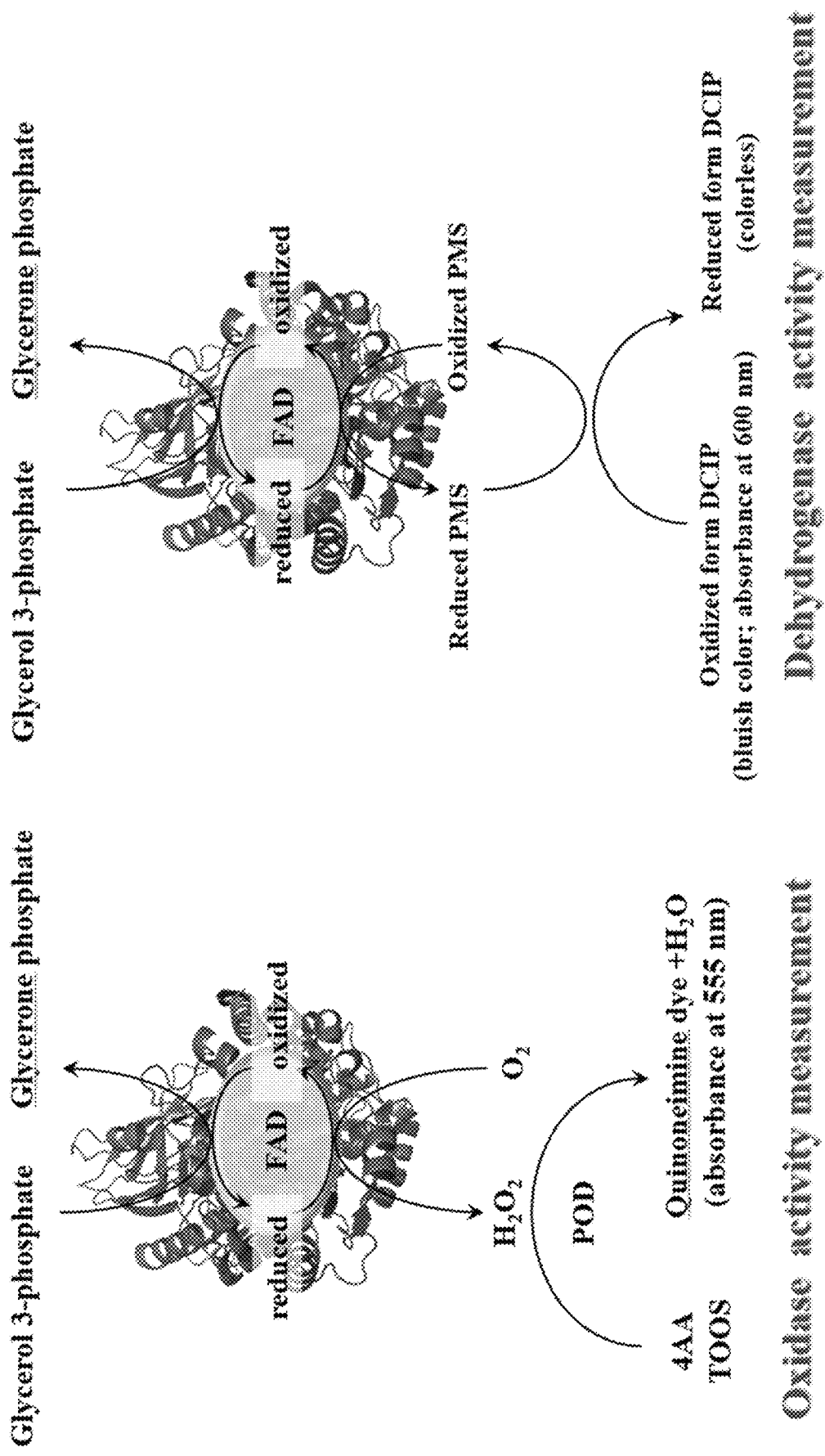

FIG. 4 illustrates oxidase and dehydroxygenase activity measurements.

Figure 5:
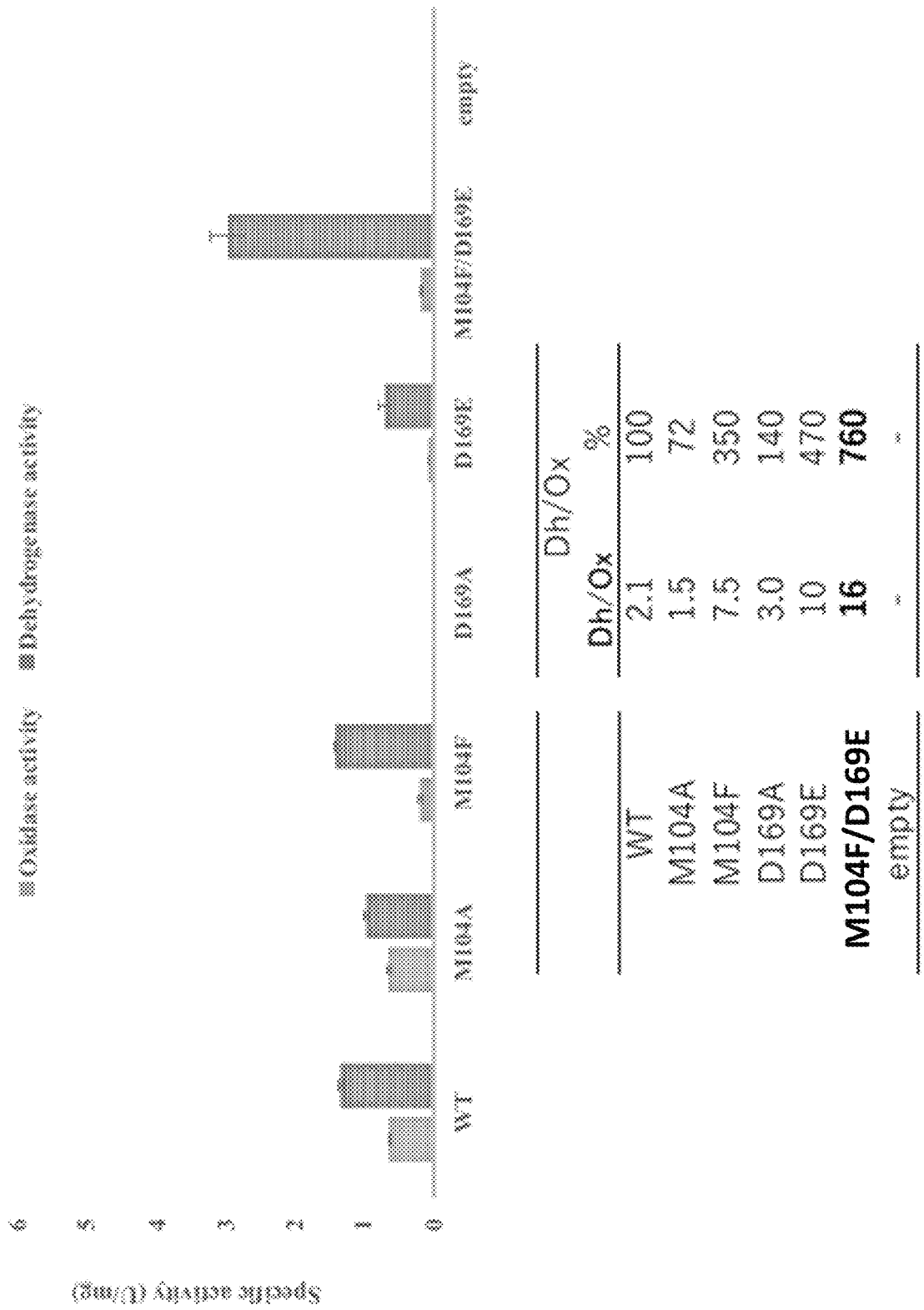

FIG. 5 illustrates oxidase and dehydroxygenase activity and Dh/Ox ratio for glycerol 3-phosphate oxidase mutants compared to wild-type.

Figure 6:
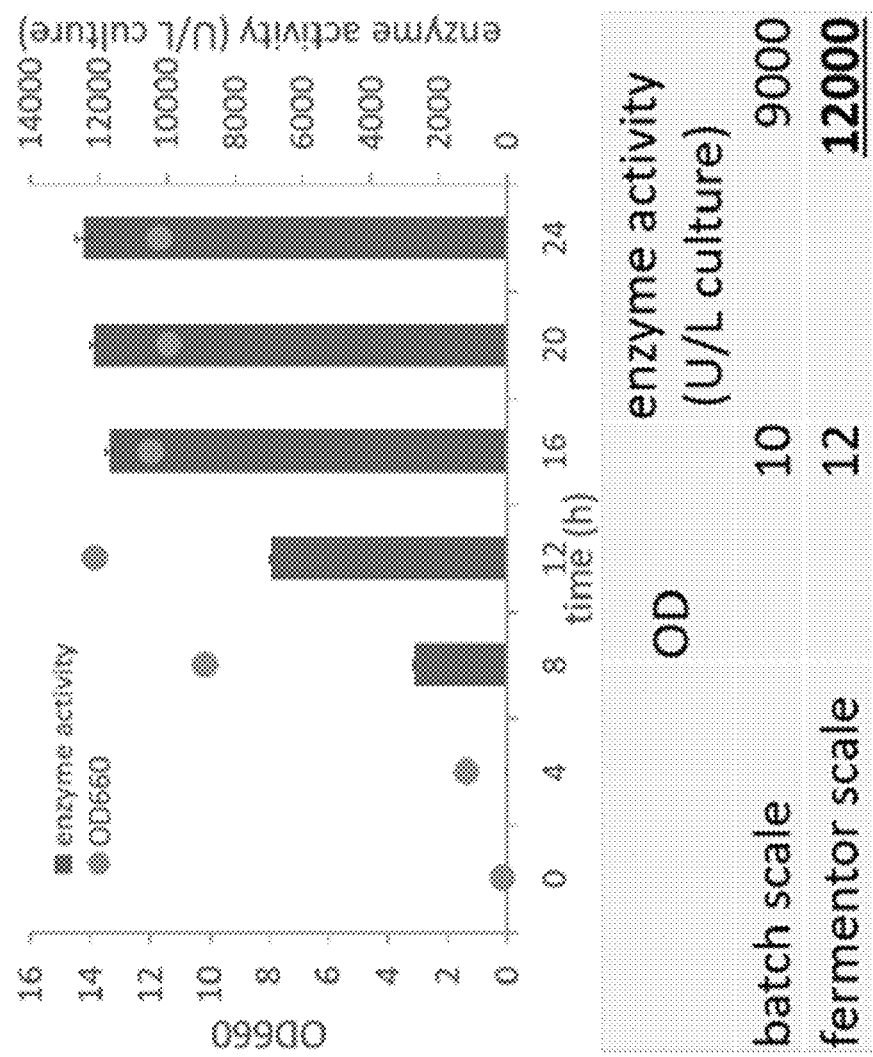

FIG. 6 illustrates representative recombinant production of GlpO using *Escherichia coli* as the host microorganism.

Figure 7:
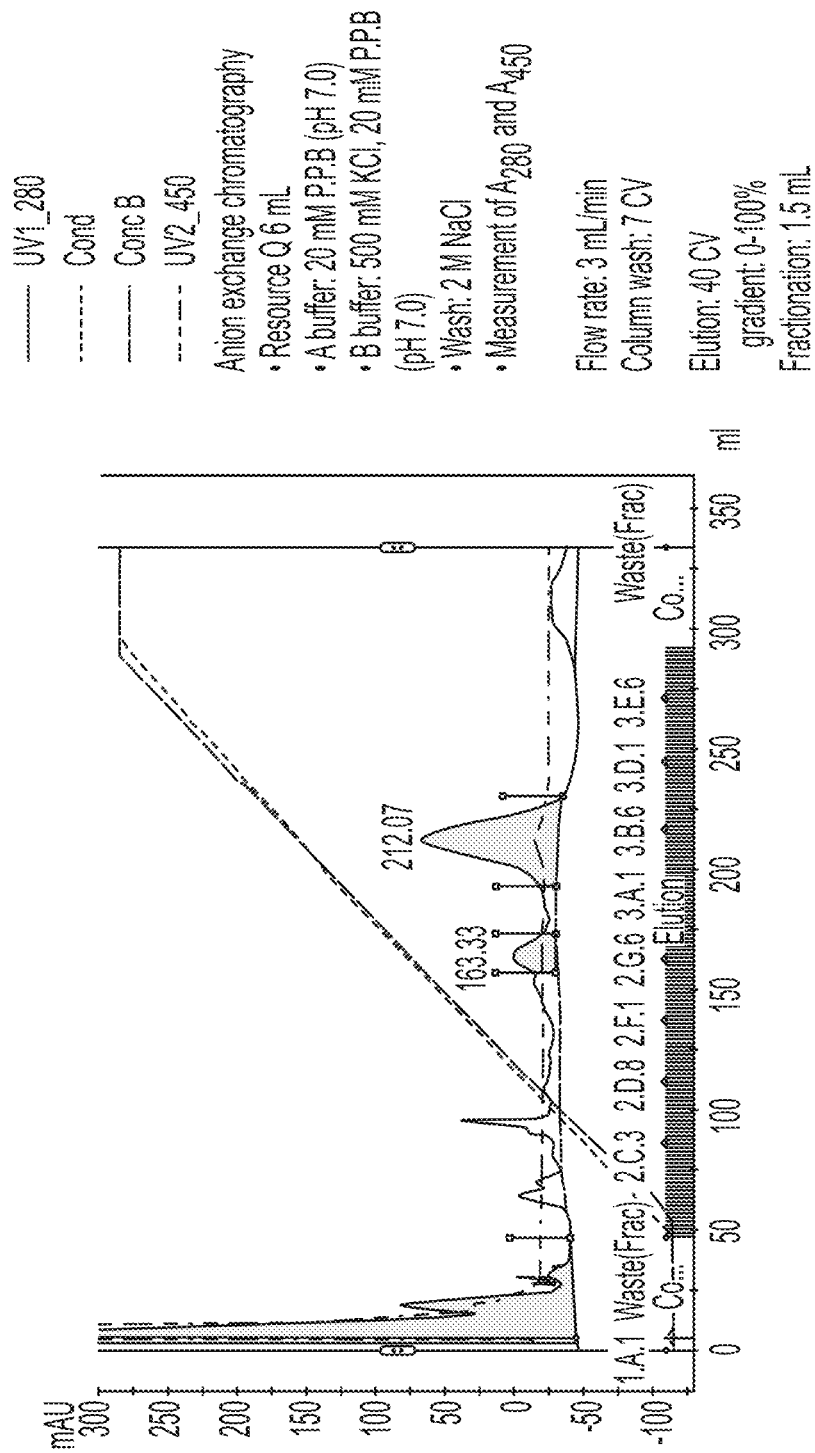

FIG. 7 illustrates representative chromatogram of recombinant GlPO purification using anion exchange chromatography.

Figure 8:
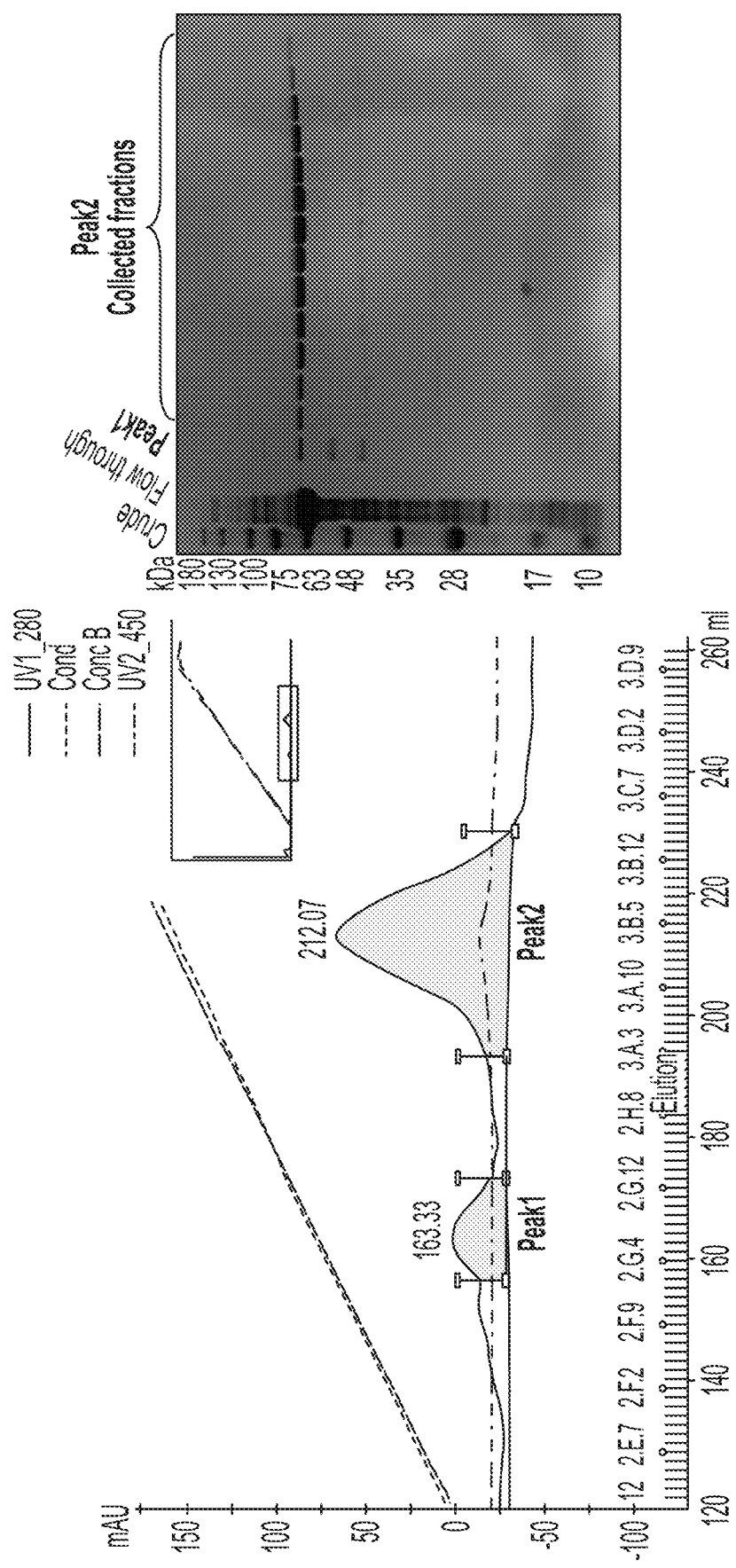

FIG. 8 illustrates representative SDS-PAGE analyses of recombinant GlPO purified with anion exchange chromatography.

Figure 9:
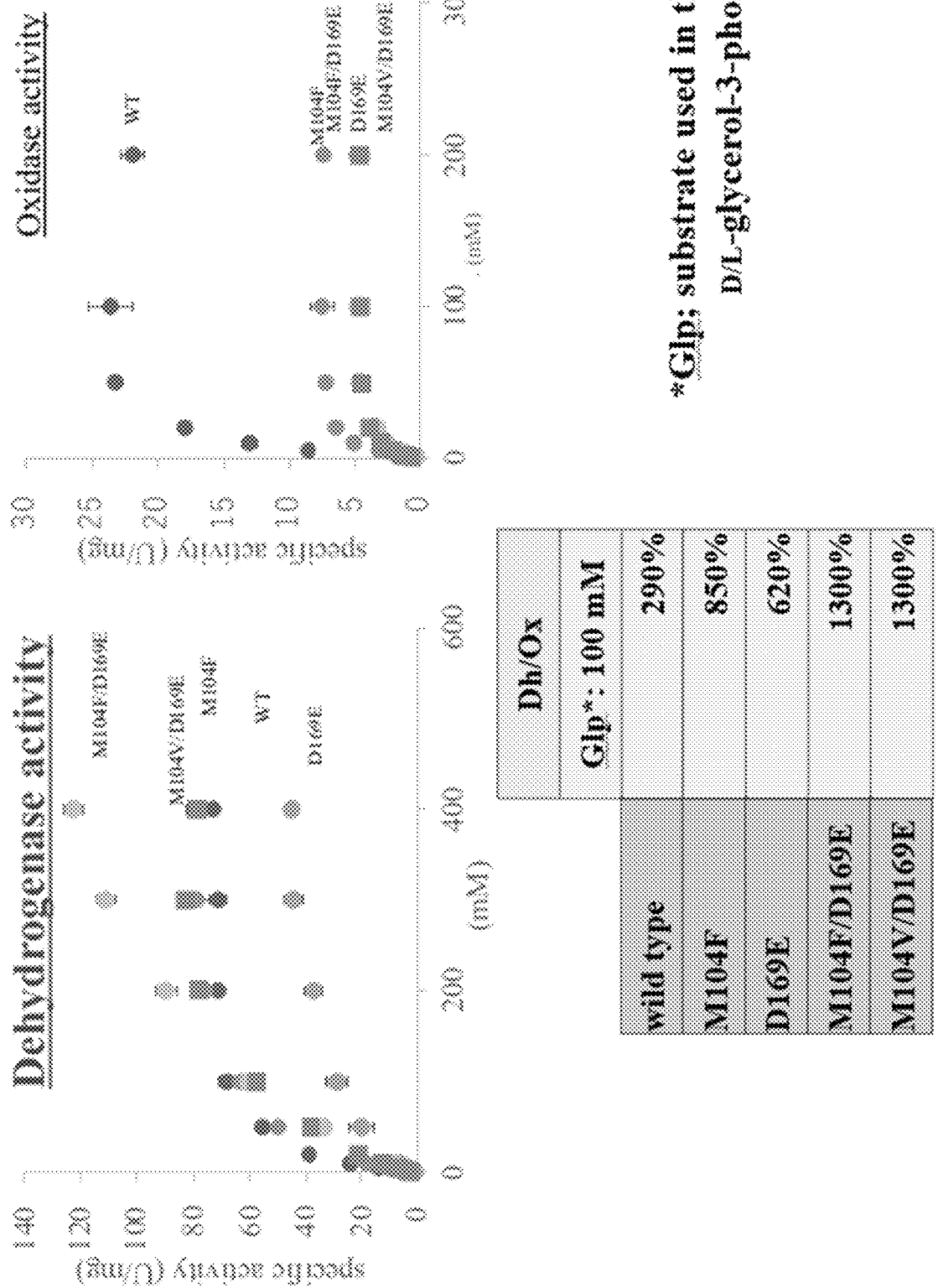

FIG. 9 illustrates oxidase and dehydroxygenase activity and Dh/Ox ratio for (D/L)-glycerol 3-phosphate oxidase mutants compared to wild-type.

Figure 10:
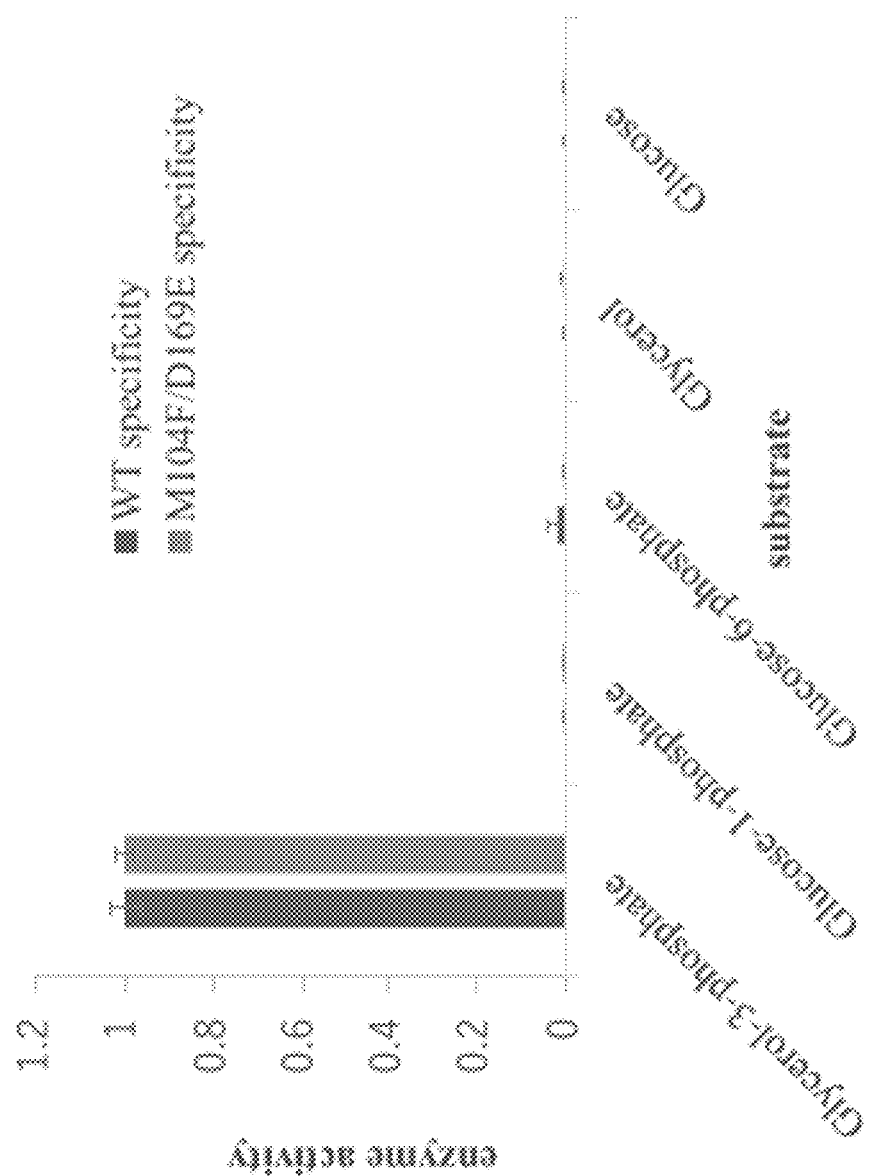

FIG. 10 illustrates substrate specificity of wild-type and mutant glycerol 3-phosphate oxidase.

Figure 11:
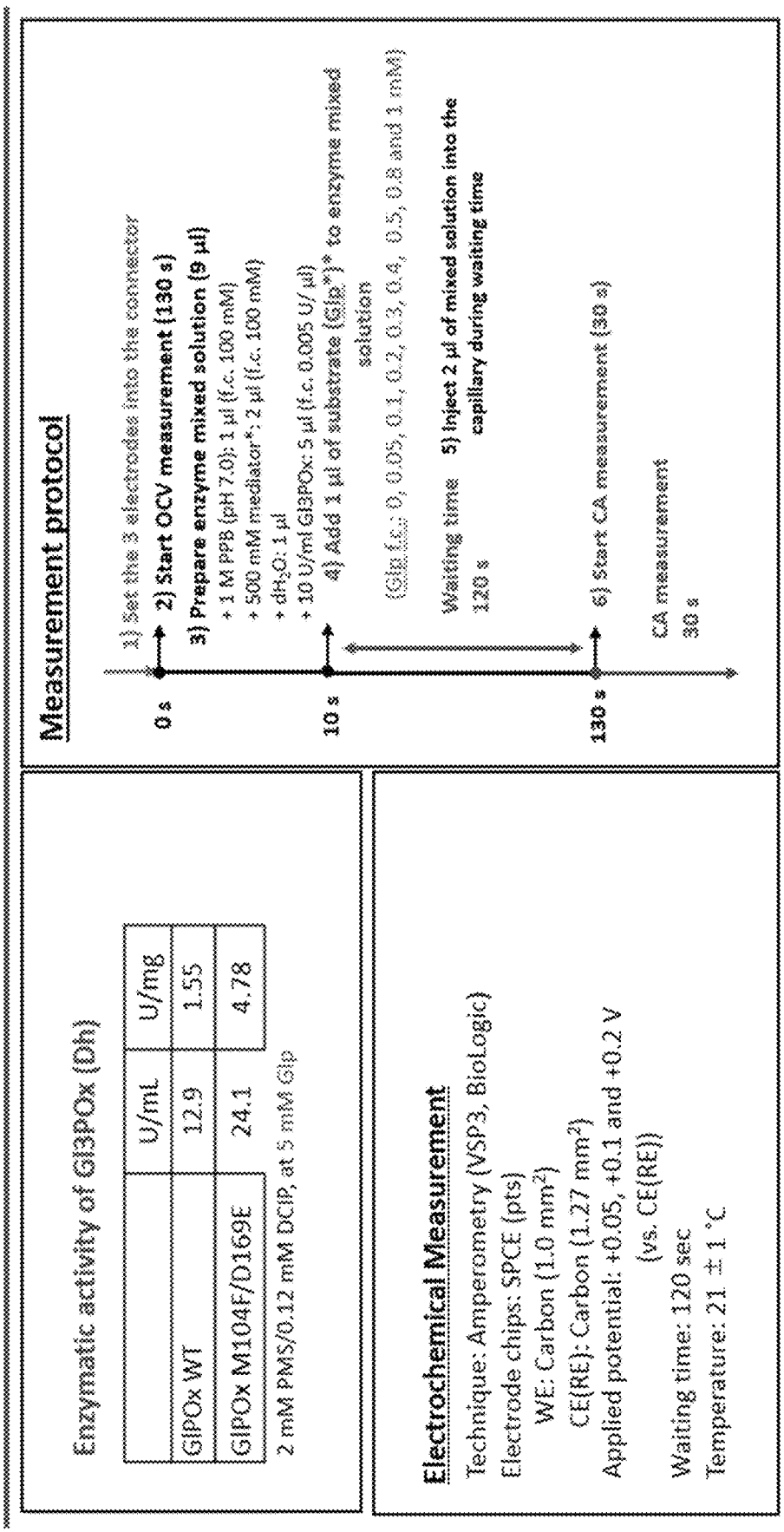

FIG. 11 illustrates an end point assay based on chronoamperometric measurement.

Figure 12:
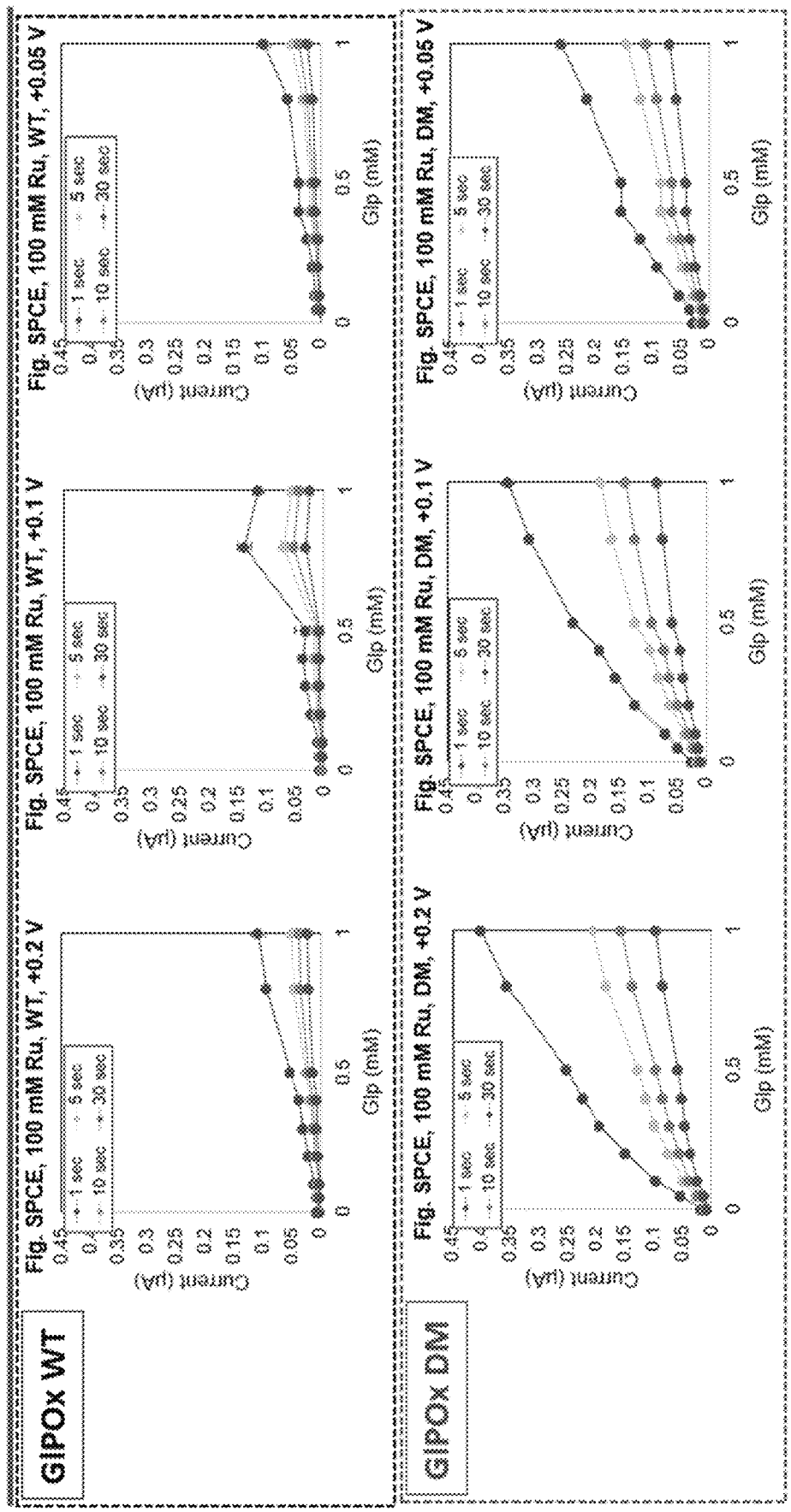

FIG. 12 illustrates results using SPCE with 100 mM Ru (+0.05, +0.1, +0.2 V (vs. CE(RE)).

Figure 13:
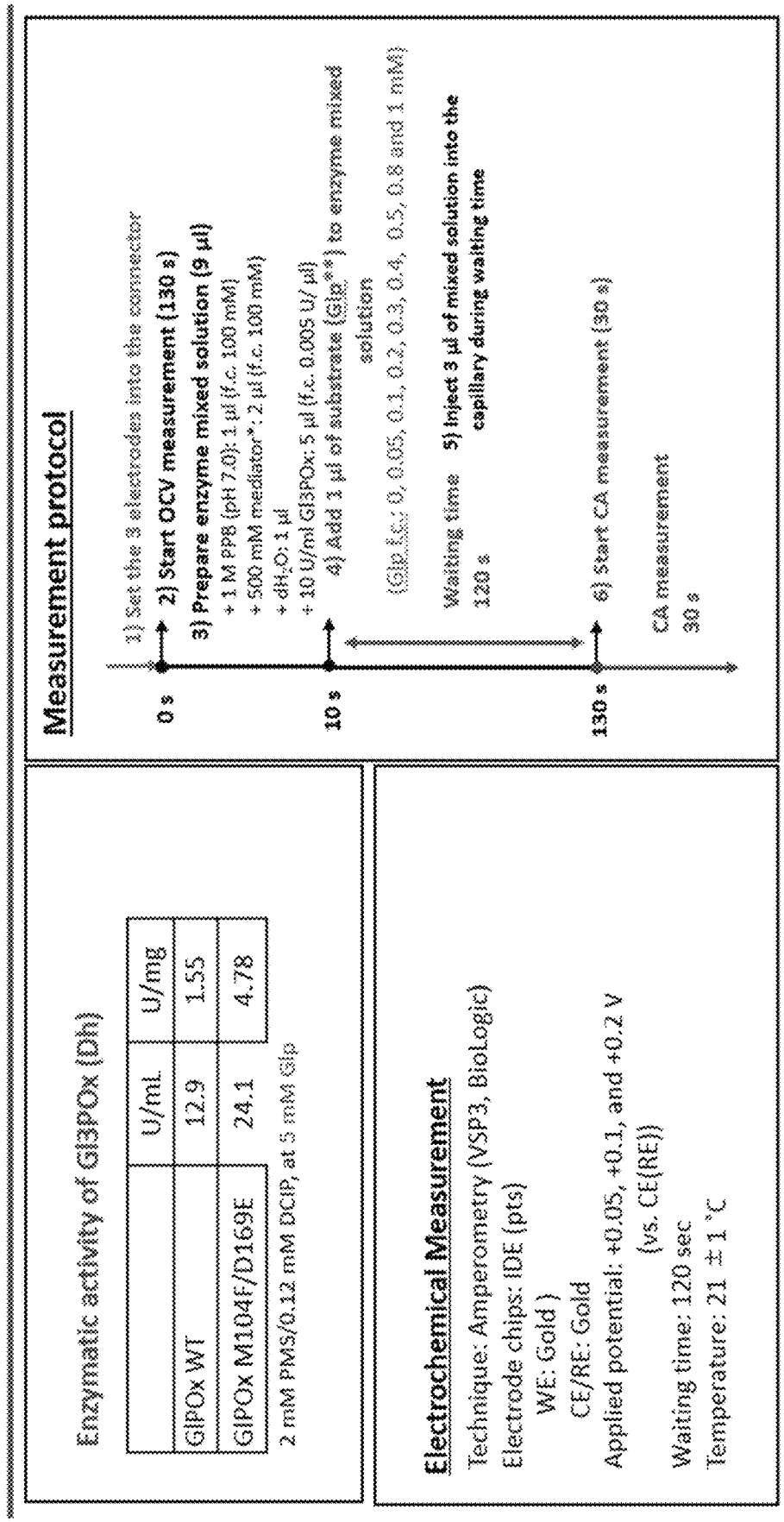

FIG. 13 illustrates an end point assay based on chronoamperometric measurement.

Figure 14:
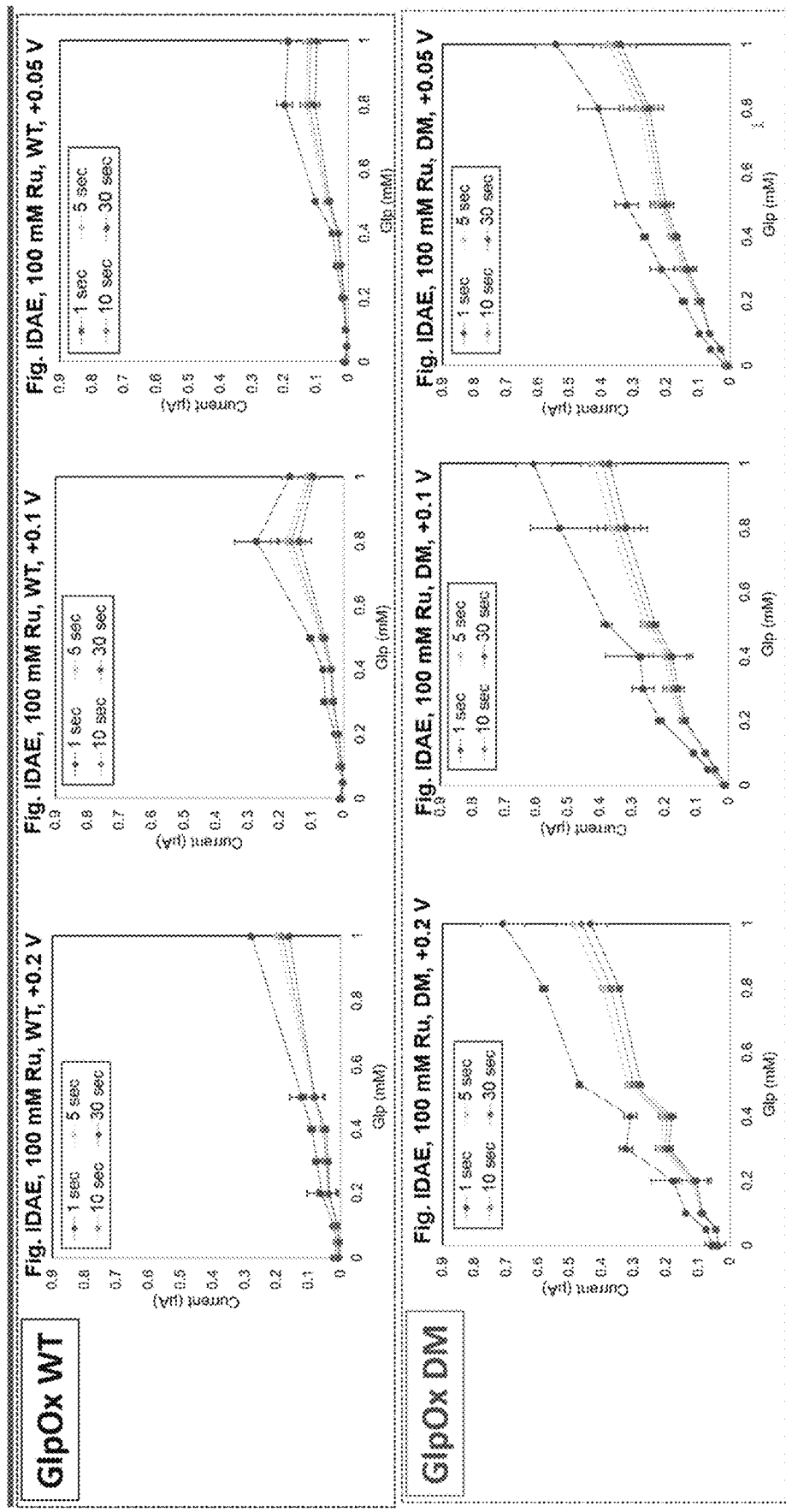

FIG. 14 illustrates results using IDAE with 100 mM Ru (+0.05, +0.1, +0.2 V (vs. CE(RE)).

Figure 15:
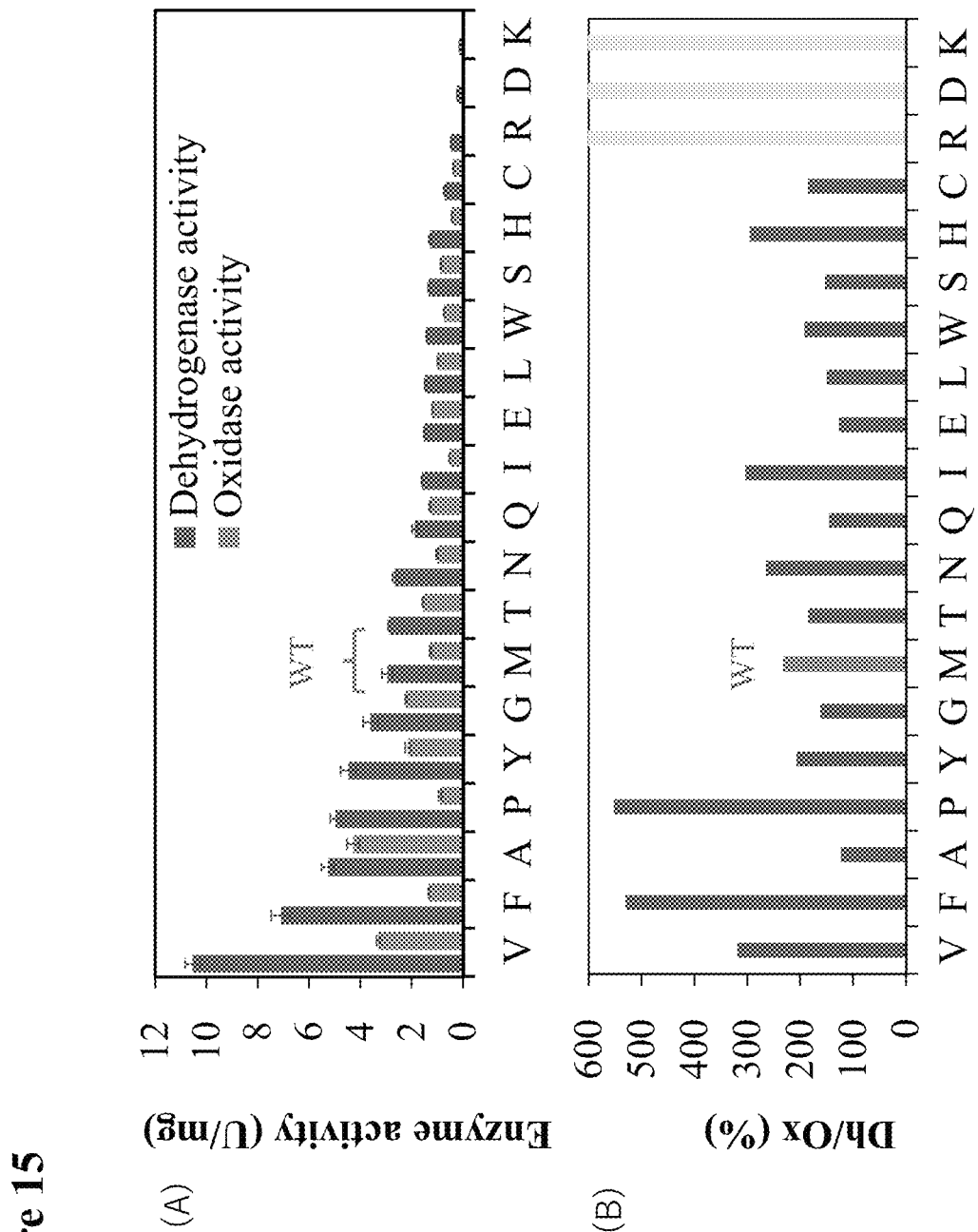

FIG. 15 illustrates saturation mutagenesis analysis at the M104 position of the glycerol 3-phosphate oxidase.

Figure 16:
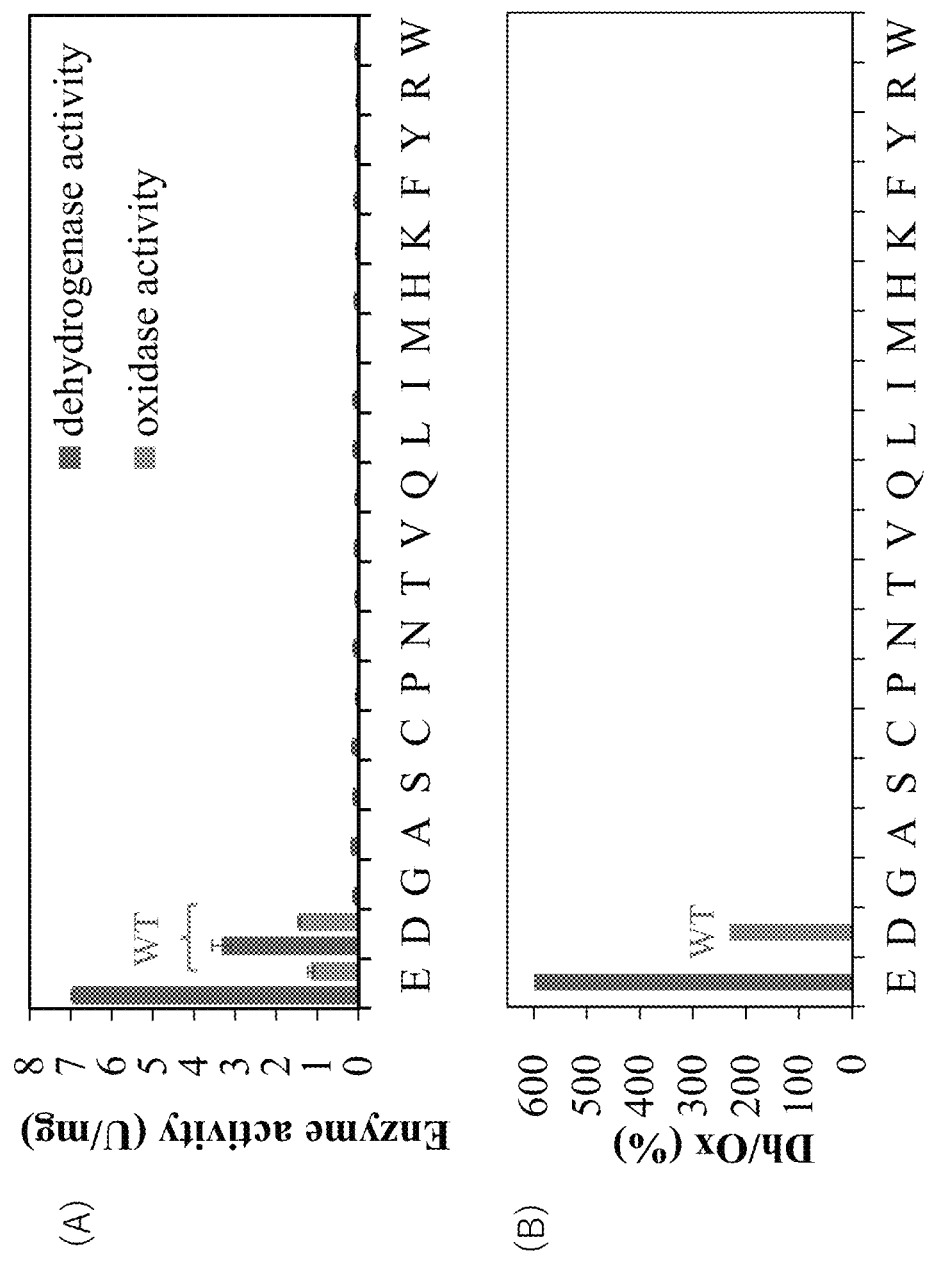

FIG. 16 illustrates saturation mutagenesis analysis at the D169 position of the glycerol 3-phosphate oxidase.

DETAILED DESCRIPTION

As described herein, engineered mutant Glycerol-3-phosphate oxidases (GlPOx) advantageously show specificity with regard to decreased activity towards oxygen while retaining catalytic activity to oxidize glycerol phosphate in the present of a mediator. As described herein, mutant GlPOx enzymes were designed based on modeling experiments to elucidate the positions for mutation where the resulting engineered enzymes exhibit the desired specificity. As described herein, it is shown that GlPOx mutants provide sensitivity and linear correlation for physiologically relevant glycerol phosphate concentrations at low levels, such as below 3 mM, which find use in use in improved detection of triglycerides in a sample. Additionally, as described herein, certain mutations surprisingly provide improved activity towards in the mutant GlPOx.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Overview

Glycerol 3-phosphate oxidase (GlPOx) is the key enzyme in the enzymatic measurement of triglyceride (TG) of whole blood for the diagnosis of hypertriglyceridemia. This enzyme belongs to the family of oxidoreductases. This enzyme acts on the CH—OH group of the donor with oxygen as acceptor and comprises cofactor FAD. Conventionally, the enzyme, GlPOx is combined with lipoprotein lipase and glycerol kinase which catalyze the liberation of glycerol phosphate, the substrate of GlPOx. Finally, GlPOx oxidizes glycerol phosphate, to liberate hydrogen peroxide to be colorimetrically measured with the combination of peroxidase colorimetric measurement. However, the current emergent requirement is to develop electrochemical sensors, similar to glucose sensors for blood glucose monitoring, where GlPOx utilizes an artificial electron acceptor (mediator) instead of oxygen for the measurement.

Inherently, GlPOx uses oxygen as the primary electron acceptor. Therefore, the response of electrochemical sensor with mediator using GlPOx is inherently affected by the oxygen. Provided herein, among other things, are: engineered GlPOx mutants which have decreased activity toward oxygen but retain enough catalytic activity to oxidize glycerol phosphate using a mediator; and, its application for an enzyme sensor to be used as triglyceride sensor. In an embodiment, the subject matter described herein is directed to an engineered GlPOx with substituted amino acid residues. In another embodiment, provided herein is an engineered GlPOx derived from *Aerococcus viridans*.

In another embodiment, the subject matter described herein is directed to enzyme electrochemical sensor strips containing the engineered GlPOx and electrode, such as, but not limited to a screen printed carbon electrode, a planar gold electrode, an interdigitated electrode array, with mediators, such as, but not limited to, nitrosoaniline, 1-methoxy-5-methyl phenazinium methyl sulfate, potassium ferricyanide, hexaammineruthenium(III) chloride, and 1-methoxy-5-ethyl phenazinium ethyl sulfate. In embodiments, the mediator is ferrocene, phenazine methosulfate, 1-methoxy PMS, 1 methoxy PES, $[Ru(NH_3)_6]Cl_3$, or WST-1.

These sensors employing engineered GlPOx have sensitivity and show linearity in physiologically relevant glycerol phosphate concentrations, even below 3 mM. In contrast, the enzyme sensor employing wild type GlPOx did not show linear correlation due to the impact of oxygen which competed with mediator during the measurement.

According to the Endocrine Society, normal blood triglyceride levels are <150 mg/dl which is about 1.7 mM. Mild hypertriglyceridemia is about 150-199 mg/dl. Moderate hypertriglyceridemia is about 200-999 mg/dl. Severe hypertriglyceridemia is about 1,000-1,999 mg/dl and very severe hypertriglyceridemia is about greater than or equal to 2,000 mg/dl. Therefore, the target concentration is about 0.5 to about 5 mM. As described herein, the engineered GlPOx mutants have the desired sensitivity for this range in particular.

II. Definitions

The term "subject" refers to a mammal (e.g., a human) in need of a triglyceride analysis. The subject may include dogs, cats, pigs, cows, sheep, goats, horses, rats, mice, non-human mammals, and humans. The term "subject" does not necessarily exclude an individual that is healthy in all respects and does not have or show signs of elevated triglycerides.

As used herein, the term "physiological conditions" refers to the range of conditions of temperature, pH, and tonicity (or osmolality) normally encountered within tissues in the body of a living human.

The term "in vitro" refers to artificial environments and to processes or reactions that occur within an artificial environment (e.g., a test tube).

The term "in vivo" refers to natural environments (e.g., a cell or organism or body) and to processes or reactions that occur within a natural environment.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers, tenths, and hundredths within the range. Similarly, where the features or aspects of the invention are described in terms of Markush groups, those skilled in the art will recognize that the invention is also thereby described in terms of any individual member or subgroup members of the Markush group.

The singular forms of the articles "a," "an," and "the" include plural references unless the context clearly dictates otherwise. For example, the term "an antigen" or "at least one antigen" can include a plurality of antigens, including mixtures thereof.

Statistically significant means p≤0.05.

Other definitions are provided below.

III. Compositions

Glycerol 3-Phosphate Oxidase Mutants

In one embodiment, provided herein is an isolated, glycerol 3-phosphate oxidase mutant that exhibits decreased oxidase (or Ox) activity when compared to a wild-type glycerol 3-phosphate oxidase while substantially retaining dehydrogenase (or Dh) activity. In another embodiment, the glycerol 3-phosphate oxidase mutant further exhibits an increased Dh activity when compared to the wild-type glycerol 3-phosphate oxidase. In embodiments, the Dh/Ox ratio is higher in a glycerol 3-phosphate oxidase mutant than wild-type glycerol 3-phosphate oxidase.

As used herein, "isolated," with respect to a polypeptide (and also a polynucleotide), means a molecule (e.g., polypeptide, protein or polynucleotide) isolated from its natural environment or prepared using synthetic methods such as those known to one of skill in the art. Complete purification is not required in either case. The molecules described herein can be isolated and purified from normally associated material in conventional ways, such that in the purified preparation the molecule is the predominant species in the preparation. At the very least, the degree of purification is such that extraneous material in the preparation does not interfere with use of the molecule in the manner disclosed herein. The molecule is at least about 85% pure; alternatively, at least about 90% pure, alternatively, at least about 95% pure; and alternatively, at least about 99% pure.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The term "wild type" refers to entities having a structure and/or activity as found in a normal (as contrasted with mutant, diseased, altered, or so forth) state or context. Wild type genes and polypeptides often exist in multiple different forms (e.g., alleles).

As used herein, "mutant," when used in connection with a polypeptide or protein such as an enzyme, means a variant containing a substitution in one or more of the amino acid residues on the polypeptide or protein at the indicated position(s). Mutant also is used for a polynucleotide encoding such a mutant polypeptide or protein.

As used herein, "a position corresponding to" means the position of an amino acid residue in a query amino acid sequence that is aligned with the amino acid residue in a reference amino acid sequence using software such as AlignX of Vector NTI with default parameters (available from Invitrogen; see, Lu & Moriyama (2004) *Brief Bioinform.* 5:378-88). Thus, "amino acid (AA) residue at a position corresponding to the position Y of the amino acid sequence set forth in SEQ ID NO: X" means the AA residue in a query amino acid sequence that is aligned with AA Y of SEQ ID NO: X when the query amino acid sequence is aligned with SEQ ID NO: X using AlignX of Vector NTI with default parameters. It should be noted that the AA Y of SEQ ID NO: X itself is also encompassed by this term.

As used herein, "oxidase activity" or "Ox activity" means an enzymatic activity of the glycerol 3-phosphate oxidase mutant to catalyze the oxidation of glycerol-3-phosphate to generate dihydrozyacetone phosphate by utilizing oxygen as an electron acceptor. The oxidase activity may be assayed by measuring the amount of generated hydrogen peroxide ($H_2O_2$) by any method known in the art such as, for example, by reagents for $H_2O_2$ detection such as 4AA/TODB/POD (4-aminoantipyrine/N,N-bis(4-sulfobutyl)-3-methylaniline disodium salt/horseradish peroxidase) or by a platinum (Pt) electrode. In the context of the relative or quantitative activity, the oxidase activity is specifically defined to be the mole amount of the substrate (triglyceride) oxidized per unit time measured by the amount of generated $H_2O_2$ at about 25° C. in 10 mM PPB, pH 7.0, 1.5 mM TODB, 2 U/ml horseradish peroxidase (POD), and 1.5 mM 4-aminoantipyrine (4AA). The formation of quinoneimine dye may be measured spectrophotometrically at 546 nm. This measurement, because it depends on oxygen, can be influenced by exposure to oxygen and the presence of dissolved oxygen.

As used herein, "dehydrogenase activity" or "Dh activity" means an enzymatic activity of the glycerol 3-phosphate oxidase mutant to catalyze the oxidation of glycerol-3-phosphate to generate dihydrozyacetone phosphate by utilizing a synthetic electron acceptor or electron mediator other than oxygen as an electron acceptor. This measurement, because it does not depend on oxygen, is less influenced by dissolved oxygen. The dehydrogenase activity may be assayed by measuring the amount of electron transferred to the mediator using, for example, mPMS/DCIP (1-methoxy-5-methylphenazinium methylsulfate/2,6-dichloroindophenol), cPES (trifluoro-acetate-1-(3-carboxypropoxy)-5-ethyl-phenanzinium), NA BM31_1144 (N,N-bis -(hydroxyethyl)-3-methoxy-nitrosoaniline hydrochloride), NA BM31_1008 (N,N-bis -hydroxyethyl-4-nitrosoaniline) and N—N-4-dimethyl-nitrosoaniline. In the context of the relative or quantitative activity, the dehydrogenase activity is specifically defined to be the mole amount of the substrate (e.g., triglyceride) oxidized per unit time measured by the amount of electron transferred to the mediator at about 25° C. in 10 mM PPB (pH 7.0), 0.6 mM DCIP, and 6 mM methoxy PMS (mPMS).

It is therefore desired to modulate GlPOx+s activity towards the electron mediator and away from oxygen. In one embodiment, the glycerol 3-phosphate oxidase mutant therefore has a reduced oxidase activity when compared to a wild-type glycerol 3-phosphate oxidase, while substantially retaining the dehydrogenase activity. In another embodiment, the glycerol 3-phosphate oxidase mutant can have an oxidase activity of about 50% or less when compared to the wild-type glycerol 3-phosphate oxidase. In another embodiment, the glycerol 3-phosphate oxidase mutant has an oxidase activity of about 40% or less, about 30% or less, about 20% or less, or about 15% or less when compared to the wild-type glycerol 3-phosphate oxidase. In another embodiment, the glycerol 3-phosphate oxidase mutant can have an oxidase activity of about 30% or less when compared to the wild-type glycerol 3-phosphate oxidase.

In addition, the glycerol 3-phosphate oxidase mutant can have a dehydrogenase activity of about 50% or more when compared to a wild-type glycerol 3-phosphate oxidase. Alternatively, the glycerol 3-phosphate oxidase mutant has a dehydrogenase activity of about 60% or more, about 70% or more, about 80% or more, about 90% or more, about 100% or more when compared to the wild-type glycerol 3-phosphate oxidase.

In the wild-type glycerol 3-phosphate oxidase, the ratio of dehydrogenase/oxidase activity is about 2.1. When dissolved oxygen is present in an assay system, electrons generated by oxidizing the substrate can be transferred to oxygen. Thus, the enzyme activity measured in the presence of an electron mediator will be greatly affected by the dissolved oxygen concentration. In certain embodiments, the glycerol 3-phosphate oxidase mutant as described herein has a ratio of dehydrogenase/oxidase activity of about 3.0 or more, about 4.0 or more, about 5.0 or more, about 6.0 or more, about 7.0 or more, about 8.0 or more, about 10.0 or more, or about 15 or more. In one embodiment, the glycerol 3-phosphate oxidase mutant as described herein has a ratio of dehydrogenase/oxidase activity of about 16.0. In certain embodiments, the glycerol 3-phosphate oxidase mutant as described herein has a ratio of dehydrogenase/oxidase activity of from about 1.0 to about 30; or from about 5 to about 25; or from about 10 to about 20; or from about 14 to about 18.

In another embodiment, the glycerol 3-phosphate oxidase mutant has a ratio of dehydrogenase/oxidase activity of about 100% or more, about 200% or more, about 300% or more, about 400% or more, about 500% or more, about 600% or more, about 700% or more, about 800% or more, about 900% or more, about 1000% or more, about 1100% or more, about 1200% or more, about 1300% or more. In another embodiment, the glycerol 3-phosphate oxidase mutant as described herein has a ratio of dehydrogenase/oxidase activity of from about 50% to about 1500%; or from about 100% to about 1500%; or from about 200% to about 1500%; or from about 300% to about 1500%; or from about 400% to about 1500%; or from about 500% to about 1500%; or from about 500% to about 1400%; or from about 500% to about 1300%; or from about 500% to about 1200%; or from about 500% to about 1100%; or from about 500% to about 1000%; or from about 600% to about 1500%; or from about 700% to about 1500%; or from about 800% to about 1500%; or from about 900% to about 1500%; or from about 1000% to about 1500%. In certain embodiments, since the dehydrogenase activity exceeds the oxidase activity, the enzyme activity of the glycerol 3-phosphate oxidase mutant will be less affected by the dissolved oxygen concentration, which is advantageous in utilizing the glycerol 3-phosphate oxidase mutant in a clinical diagnosis with a blood sample.

It should be understood that the numbering of the amino acid sequence for glycerol 3-phosphate oxidase herein begins at an initial Met and that the glycerol 3-phosphate oxidase mutant described herein may or may not have the signal peptide.

In one embodiment, the glycerol 3-phosphate oxidase is from *Aerococcus viridans* and has the following sequence:

(SEQ ID NO: 1)
MSKLSFKYRKETVEQLKENQYDLFIIGGGITGAGVA

IQAAASGLKTALVDMQDFSEGTSSRSTKLVHGGIR

YLKNFDLEVVSDTVTERATVHNIAPHIPQPDPMLM

PLYDEPKVTFNPLRLQIAMDIYDSLAGVKDSQYAN

EMLSKDEVLSRQPDLMAEGLIGGGKYLDFNNNDSR

LVIENIKQANDDGADLLSHAKVVGFEYENDKIVAV

KVEDLLSGETFTVKSHVVINTTGPWSDTIRQLDGS

DKKPAQMRPTKGVHFVVDKSKLTVSQPIYFDTGEQ

DGRMVFVLPRENKTYFGTTDTDYTGDFEHPTVTQE

DVDYLLRVVNHRFPNANLSINDIEASWAGLRPLID

SNNASDYNGGDAGRLSERTFDELVALFDDYSKDKV

ERSTVEDKLQDLGSNTSERGDGSPSSVSRGSDLSV

APSGLFTLAGGKITDYRKMAKGAMERIIPVVTDIT

GKSYELVQSSTYPISGGQFDPNSYETAMEKFANVG

VARGLTYGQSLNLAKLYGSNIVINRVISYLPVAKE

YAAKYDYPVDIAVSLIYALEEEGVYTPLDFFARRT

TFMLFQHDKMLAVKEAVSQTIVDYFGLDQATADQQ

KTALDEEIAKAELQYLK

In one embodiment, the glycerol 3-phosphate oxidase comprises SEQ ID NO: 1. In embodiments, provided herein is a glycerol 3-phosphate oxidase mutant comprising a sequence having at least 70%, 80%, 85%, 90%, 95%, 96%, 97%, 98%, or 99% sequence identity to SEQ ID NO: 1.

In embodiments, provided herein is a glycerol 3-phosphate oxidase mutant comprising a sequence having at least 90% sequence identity to SEQ ID NO: 1 provided at least one of positions 99 to 109 or positions 164-174 is different from the amino acid occupying the corresponding position in SEQ ID NO: 1. In an embodiment, provided herein is a glycerol 3-phosphaste oxidase modified in at least one position corresponding to 104 or 169 of SEQ ID NO: 1. In embodiments, provided herein is a glycerol 3-phosphate oxidase mutant comprising SEQ ID NO: 1 and provided at least one of positions 104 or positions 169 is different from the amino acid occupying the corresponding position in SEQ ID NO: 1.

In embodiments, provided herein is a glycerol 3-phosphate oxidase mutant, comprising a modification at position 104 of the amino acid sequence set forth in SEQ ID NO: 1, wherein the modification comprises a substitution of the amino acid residue Met with an amino acid residue selected from Ala, Arg, Asn, Asp, Cys, Glu, Gln, Gly, His, Ile, Leu, Lys, Phe, Pro, Ser, Thr, Trp, Tyr, and Val. In embodiments, provided herein is a glycerol 3-phosphate oxidase mutant, comprising a modification at position 104 of the amino acid sequence set forth in SEQ ID NO: 1, wherein the modification comprises a substitution of the amino acid residue Met with an amino acid residue selected from Phe, Pro, and Val. In embodiments, provided herein is a glycerol 3-phosphate oxidase mutant, comprising a modification at position 104 of the amino acid sequence set forth in SEQ ID NO: 1, wherein the modification comprises a substitution of the amino acid residue Met with an amino acid residue selected from Phe, Pro and Val. In embodiments, provided herein is a glycerol 3-phosphate oxidase mutant, comprising a modification at position 104 of the amino acid sequence set forth in SEQ ID NO: 1, wherein the modification comprises a substitution of the amino acid residue Met with an amino acid residue selected from Ala and Phe. In embodiments, provided herein is a glycerol 3-phosphate oxidase mutant, comprising a modification at position 104 of the amino acid sequence set forth in SEQ ID NO: 1, wherein the modification comprises a substitution of the amino acid residue Met with Phe.

In embodiments, provided herein is a glycerol 3-phosphate oxidase mutant, comprising a modification at position 169 of the amino acid sequence set forth in SEQ ID NO: 1, wherein the modification comprises a substitution of the amino acid residue Asp with an amino acid residue selected from Ala, Arg, Asn, Cys, Glu, Gln, Gly, His, Ile, Leu, Lys, Met, Phe, Pro, Ser, Thr, Trp, Tyr, and Val. In embodiments, provided herein is a glycerol 3-phosphate oxidase mutant, comprising a modification at position 169 of the amino acid sequence set forth in SEQ ID NO: 1, wherein the modification comprises a substitution of the amino acid residue Asp with an amino acid residue Glu.

In an embodiment, provided herein is a glycerol 3-phosphate oxidase mutant which harbors an amino acid substitution or substitutions selected from the group consisting of Met104Ala, Met104Phe, Met104Val, Asp169Ala, Asp169Glu, Met104Pro, and Met104Phe/Asp169Glu. In an embodiment, provided herein is a glycerol 3-phosphate oxidase mutant which harbors an amino acid substitution or substitutions selected from the group consisting of Met104Phe, Met104Val, Asp169Glu, Met104Pro, and Met104Phe/Asp169Glu. In an embodiment, provided herein is a glycerol 3-phosphate oxidase mutant which harbors an amino acid substitution or substitutions selected from the group consisting of Met104Phe, Met104Val, Asp169Glu, and Met104Phe/Asp169Glu. In an embodiment, provided herein is a glycerol 3-phosphate oxidase mutant which harbors an amino acid substitution or substitutions selected from the group consisting of Met104Phe, Met104Val, Asp169Glu, and Met104Phe/Asp169Glu.

"Increased" and "reduced" in the context of enzymatic activity refer to a higher or lower level of enzymatic activity compared to a reference enzyme, respectively. In an embodiment, said reference enzyme is a wild-type enzyme. In an embodiment, an enzyme's activity is calculated in terms of U/mg, where U is the amount of enzyme that catalyzes the reaction of 1 µmol of substrate per minute. In embodiments, enzyme activity is determined at a temperature between about 20 and about 40° C. In embodiments, enzyme activity is determined at about 37° C. In certain embodiments, the increase or reduction may be a difference of from about 1% to about 70%; or from about 1% to about 60%; or from about 1% to about 50%; or from about 1% to about 40%; or from about 1% to about 30%; or from about 1% to about 20%; or from about 1% to about 10%.

"Mutant" in the context of proteins refers to a protein with at least one mutation (or modification) compared to a protein having a wild-type sequence. In an embodiment, said mutation is addition, substitution, or deletion of an amino acid. In an embodiment, said mutation is a substitution.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" refers to the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Amino acid | 3-letter code | 1-letter code | Polar/Nonpolar | Charge | Hydrophobicity index |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

Glycerol 3-Phosphate Oxidase Mutant-Encoding Polynucleotides

In one embodiment, provided herein is an isolated polynucleotide that encodes a for glycerol 3-phosphate oxidase mutant as described herein.

The terms "nucleic acid" and "polynucleotide," used interchangeably herein, refer to polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The polynucleotide encoding the wild-type glycerol 3-phosphate oxidase may be cloned from the genome of respective organisms using PCR or other known techniques. Then, mutations may be introduced by techniques such as site-directed mutagenesis, PCR mutagenesis or any other known techniques. The amino acid residue to be mutated may be identified using any software for sequence alignment available in the art. Alternatively, polynucleotides coding for the for glycerol 3-phosphate oxidase mutant may be prepared by PCR using a series of chemically synthesized oligonucleotides, or fully synthesized. Examples of nucleotide sequences for the glycerol 3-phosphate oxidase mutant can include, but are not limited to, those encoding SEQ ID NO: 1 modified at least at one of a position corresponding to position 104 and 169 of SEQ ID NO: 1.

Vectors and Host Cells

In another embodiment, provided herein is a vector comprising the glycerol 3-phosphate oxidase mutant-encoding polynucleotide or a host cell expressing the vector comprising the glycerol 3-phosphate oxidase mutant-encoding polynucleotide. The glycerol 3-phosphate oxidase mutant may be prepared by inserting a mutant polynucleotide into an appropriate expression vector and introducing the vector into an appropriate host cell, such as, for example, *Escherichia coli*. The transformant is cultured and the glycerol 3-phosphate oxidase mutant expressed in the transformant may be collected from the cells or culture medium by any known technique.

In embodiments, the recombinant glycerol 3-phosphate oxidase mutant thus obtained may be purified by any of the known purification techniques including, but not limited to, ion exchange column chromatography, affinity chromatography, liquid chromatography, filtration, ultrafiltration, salt precipitation, solvent precipitation, immunoprecipitation, gel electrophoresis, isoelectric electrophoresis and dialysis.

In embodiments, provided herein are isolated or purified polypeptides, proteins and polynucleotides for a glycerol 3-phosphate oxidase mutant, a vector comprising the polynucleotide encoding the glycerol 3-phosphate oxidase mutant, an isolated host cell transformed with such a vector, and a method for preparing the glycerol 3-phosphate oxidase mutant by culturing the transformant, collecting and purifying the glycerol 3-phosphate oxidase mutant from the culture.

IV. Devices

In another embodiment, provided herein is a device for assaying triglyceride in a sample, where the device includes a glycerol 3-phosphate oxidase mutant as described herein and optionally an electron mediator.

In one embodiment, the device is a biosensor test strip having at least the glycerol 3-phosphate oxidase mutant as described herein as a reagent. The assay device may have a similar structure as any conventional, commercially available electrochemical (e.g., amperometric) biosensor test strip for monitoring the blood triglyceride level. One example of such a device has two electrodes (i.e., a working electrode and a reference or counter electrode) positioned on an insulating substrate, a reagent port and a sample receiver. The reagent port contains the glycerol 3-phosphate oxidase mutant and the electron mediator. In an embodiment, the electron mediator is nitrosoaniline, 1-methoxy-5-methyl phenazinium methyl sulfate, potassium ferricyanide, hexaammineruthenium(III) chloride, or 1-methoxy-5-ethyl phenazinium ethyl sulfate.

In one embodiment, a sample, such as a blood sample, is added to the sample receiver, and triglyceride contained in the sample will react with the glycerol 3-phosphate oxidase mutant and the electron mediator to generate a current, which is indicative of the amount of triglyceride in the sample. The sensitivity and linearity provided by the GlPOx mutant desirably provides improved accuracy and precision on the amount of triglyceride present in the sample.

In another embodiment, optical detection technologies might be used. Typically, such optical devices are based on color changes that occur in a reagent system comprising an enzyme, an electron mediator and an indicator. The color changes can be quantified using fluorescence, absorption or remission measurements. Examples of optical devices for determining enzyme substrate concentration are known in, for example, U.S. Pat. Nos. 7,008,799; 6,036,919 and 5,334,508.

In another embodiment, provided herein is an enzyme electrode having at least the glycerol 3-phosphate oxidase mutant immobilized on the electrode. In another embodiment, provided herein is an enzyme sensor for assaying triglyceride comprising an enzyme electrode as described herein as a working electrode. The concentration of triglyceride in a sample may be determined by measuring the amount of electrons generated by the enzyme reaction. In embodiments, a sensor system such as carbon (C) electrode, metal electrode, or Pt electrode is used.

In one embodiment, the glycerol 3-phosphate oxidase mutant can be immobilized on electrodes. Examples of means for immobilizing molecules such as the glycerol 3-phosphate oxidase mutant include, but are not limited to, cross-linking, encapsulating into a macromolecular matrix, coating with a dialysis membrane, optical cross-linking polymer, electroconductive polymer, oxidation-reduction polymer, and any combination thereof.

In embodiments, the electrode is a screen printed carbon electrode, a planar gold electrode, or an interdigitated electrode array.

When the measurement is conducted in an amperometric system using a Carbon electrode, gold (Au) electrode or Pt electrode provided with an immobilized enzyme is used as a working electrode, together with a counter electrode (such as a Pt electrode) and a reference electrode (such as a Ag/AgCl electrode). The electrodes can be inserted into a buffer containing a mediator and kept at a predetermined temperature.

A predetermined voltage can be applied to the working electrode, and then a sample is added and an increased value in electric current is measured. It is generally also possible to use so-called two-electrode systems with one working electrode and one counter or pseudo-reference electrode.

In another embodiment, triglycerides may be assayed using an immobilized electron mediator in an amperometric system using a C electrode, Au electrode or Pt electrode. The enzyme, such as a glycerol 3-phosphate oxidase mutant, can be immobilized on the electrode together with an electron mediator such as potassium ferricyanide, ferrocene, osmium derivative, or phenazine methosulfate in a macromolecular matrix by means of adsorption or covalent bond to prepare a working electrode.

In one embodiment, the working electrode can be inserted into buffer together with a counter electrode (such as a Pt electrode) and a reference electrode (such as a Ag/AgCl electrode), and kept at a predetermined temperature. As indicated above, a predetermined voltage can be applied to the working electrode, and then the sample is added and increased value in electric current is measured.

V. Kits

In another embodiment, provided herein are kits for assaying triglycerides in a sample, where the kits include at least a glycerol 3-phosphate oxidase mutant as described herein and optionally an electron mediator.

Additionally, the kits can include a buffer necessary for the measurement, an appropriate electron mediator and, if necessary, further enzymes such as lipoprotein lipase or glycerol kinase, a standard solution of triglyceride for preparing a calibration curve and an instruction for use. The glycerol 3-phosphate oxidase mutant may be provided in various forms such as, for example, a freeze-dried reagent or a solution in an appropriate storage solution.

Any or all of the kit reagents can be provided within containers that protect them from the external environment, such as in sealed containers. Positive and/or negative controls can be included in the kits to validate the activity and correct usage of reagents employed in accordance with the inventive concept. Controls can include samples known to be either positive or negative for the presence of a predetermined concentration of triglyceride.

VI. Methods

The glycerol 3-phosphate oxidase mutants disclosed herein can be used in various methods. For example, they can be used in methods of assaying triglyceride in a sample from a subject.

The method can include at least a step of contacting the sample with the glycerol 3-phosphate oxidase mutant and a step of measuring the amount of glycerol 3-phosphate oxidized by the glycerol 3-phosphate oxidase mutant as described above and further below. In an embodiment, the glycerol 3-phosphate oxidized by glycerol 3-phosphate oxidase mutant is L-glycerol 3-phosphate. In one embodiment, the glycerol 3-phosphate oxidase mutant reacts with the L-form of glycerol 3-phosphate. In one embodiment, the glycerol 3-phosphate oxidase mutant reacts with the L-form of glycerol 3-phosphate and does not react with the D-form of glycerol 3-phosphate. In embodiments, the sample comprises enzymes that hydrolyze triglyceride into glycerol, such as but not limited to lipoprotein lipase. In embodiments, the glycerol is phosphorylated by using enzyme, glycerol kinase, to produce glycerol 3-phosphate. In embodiments, the formed glycerol 3-phosphate will be catalyzed by the glycerol 3-phosphate oxidase mutant.

Additionally, provided herein is a method of producing a glycerol 3-phosphate oxidase mutant disclosed herein. In embodiments, a method of producing a glycerol 3-phosphate oxidase mutant comprising transforming a host cell with the vector of comprising an isolated polynucleotide encoding a glycerol 3-phosphate oxidase mutant provided herein and collecting the glycerol 3-phosphate oxidase mutant. In embodiments, the vector is a plasmid. In embodiments, a method of producing a glycerol 3-phosphate oxidase mutant comprising transforming a host cell with the vector of comprising an isolated polynucleotide encoding a glycerol 3-phosphate oxidase mutant provided herein, culturing the host cell, and collecting and purifying the glycerol 3-phosphate oxidase mutant from the culture.

The disclosed subject matter is further described in the following non-limiting Examples. It should be understood that these Examples, while indicating preferred embodiments of the subject matter, are given by way of illustration only.

EXAMPLES

Example 1: Preparation of Glycerol 3-Phosphate Oxidase Mutants

*Escherichia coli* BL21 (DE3) were transformed with expression vectors inserted with the structural gene of *Aerococcus viridans* derived GlPOx (AvGlPOx) wild type (SEQ ID NO: 1) or M104V/D169E mutants and were precultured in 3.0 mL LB medium (50 μg/mL Km) at 37° C. for 12 h, 170 rpm. The preculture medium (1.0 mL) was inoculated with Auto-induction medium (100 mL) (50 μg/mL Km) at 30° C., 150 rpm, 36 h. After harvesting, the wet cells were suspended with 3 mL 20 mM P.P.B buffer (pH 7.0) containing 4 mM 4-(2-aminoethyl) benzenesulfonyl fluoride hydrochloride (aEBSF) for 1 g wet cell and disrupted by French pressure cell press. Cell disruption solution was centrifuged (4° C., 10,000 g, 20 min) to separate the cell debris (insoluble fraction) and supernatant. Supernatant was centrifuged (4° C., 106,000 g, 1 h) to remove the membrane fraction and supernatant was collected as soluble fraction (crude enzyme). After dialyzing the crude enzyme with 20 mM P.P.B buffer (pH 7.0), anion exchange chromatography was used to purify the enzyme.

For purification, Resource Q (anion exchange chromatography column) 6 mL column was used and purification buffer was 20 mM P.P.B buffer (pH 7.0) (A buffer) and 20 mM P.P.B buffer (pH 7.0) adding 0.5 M KCl (B buffer). While increasing the concentration of B buffer, the enzyme was eluted to each fraction and each fraction was checked by simple activity assay. The fraction showing enzyme activity was collected and dialyzed with 20 mM P.P.B buffer (pH 7.0). The collected fraction was concentrated by Amicon Ultra 50 K for 20 times for the purified enzyme. A Bradford assay was used for protein determination with BSA as the standard. SDS-PAGE and non-reducing SDS-PAGE analysis were performed to confirm the expression of these enzymes.

Example 2: Analysis of Enzymatic Activity of Glycerol 3-Phosphate Oxidase Mutants GlPOx dehydrogenase activity was measured with PMS/DCIP system at 25° C., (final concentration; f.c. 100 mM P.P.B. pH 7.0, 0.06 mM DCIP, 2 mM PMS, various conc. of sodium DL-glycerol-3-phosphate, and the purified enzyme). One unit of enzyme activity is defined as the amount of enzyme which catalyzes the reduction of 1 μmol DCIP per min at 25° C. (The absorbance change at 600 nm derived from oxidized DCIP was measured with spectrophotometer). The oxidase activity was measured with 4AA/TOOs system at 25° C. (f.c. 100 mM P.P.B. pH 7.0, 1.5 mM 4AA, 1.5 mM TOOS, various conc. of sodium DL- glycerol-3-phosphate, and the purified enzyme). One unit of enzyme activity is defined as the amount of enzyme which catalyzes the production of 1 μmol quinone per min at 25° C. (The absorbance changes at 555 nm derived from quinone were measured with spectrophotometer). Substrate specificity was evaluated by comparing the enzyme activity using Glp, Glucose-1-phosphate, Glucose-6-phosphate, glycerol and glucose as substrate.

Substitutions of amino acid residues may disrupt the crystal structure and or enzyme activity of 3-phosphate oxidase. Alanine is small and unlikely to interact with side chains and disrupt crystal structure or enzyme activity. Unexpectedly, a phenylalanine substitution at position 104 which is larger and more likely to interact with side chains also resulted in a 3-phosphate oxidase mutant with preserved enzyme activity.

The oxidase and dehydrogenase activity of the 3-phosphate oxidase mutants were measured for M104A, M104F, D169A, D169E, M104P, and M104F/D169E compared to wild-type glycerol 3-phosphate oxidase. The mutants were prepared according to the procedure detailed in Example 1. The results and the Dh/Ox ratio are shown in FIG. 5. M104F, D169E, M104P, and M104F/D169E double mutant showed lower oxidase activity than wild type glycerol 3-phosphate oxidase. M104F and M104F/D169E double mutant showed higher dehydrogenase activity than wild-type glycerol 3-phosphate oxidase. D169A showed little to no oxidase or dehydrogenase activity.

Wild-type glycerol 3-phosphate oxidase Dh/Ox ratio was 2.1. M104F had a higher Dh/Ox ratio than wild-type at 7.5 and D169E had a Dh/Ox ratio of 10. M104F/D169E double mutant had a Dh/Ox of 16. The ratio of the dehydrogenase activity to the oxidase activity was 100% in the wild-type, whereas this ratio was improved to 760% in M104F/D169E double mutant, 350% in M104F, and 470% in D169E.

Similarly, in another experiment, oxidase and dehydrogenase activity of the glycerol 3-phosphate oxidase mutants were measured for M104F, D169E, M104F/D169E, M104V/D169E compared to wild-type glycerol 3-phosphate oxidase. The results and the Dh/Ox ratio are shown in FIG. 9. All mutants showed a higher Dh/Ox ratio than wild-type glycerol 3-phosphate oxidase.

Example 3: Investigation of GlpOx Met104Phe/Asp169Glu (Double Mutant; DM) in Electrochemical Sensing Enzyme electrochemical sensing of D/L-glycerol-3-phosphate (Glp) was investigated using either wild type *A.viridans* GlPOx (GlPOx WT) or GlpOx Met104Phe/Asp169Glu (M104F/D169E; double mutant; DM) using screen printed carbon electrode (SPCE) as the electrode. All experiments were carried out using a racemic substrate. The experimental procedures are shown in FIG. 11. In all conditions, 0.005 U/μl of either GlPOxWT or GlPOxDM was used. For the substrate several concentrations of Glp was used together with electron mediator, Hexaammine ruthenium(III) chloride (CAS #14282-91-8), (Ru), and chronoamperometric measurements were carried out by applying potential; 0.05V, 0.1V or 0.2V versus counter electrode, and current was monitored at 1 sec, 5 sec, 10 sec and 30 sec after potential application (sampling time). The observed currents are plotted against Glp concentration to see Glp-dependent catalytic current. The results are shown in FIG. 12. When the enzyme electrochemical sensing of Glp was carried out using GlPOx WT, the observed current increased with increased Glp concentration in all sampling time. However, the measurement of Glp concentrations lower than 0.5 mM was not possible. This was due to the fact that electron transfer from the reduced cofactor of the enzyme which was formed by oxidation of Glp (reduced FAD of GlPOx WT) to the oxygen was the dominant mode of electron transfer, which is less preferable than electron transfer to electron mediator Ru. In addition, at all concentrations, the current was lower than 0.1 μA, and it was therefore difficult to monitor Glp concentration using GlpOx WT as the enzyme. To the contrary, when the enzyme electrochemical sensing of Glp was carried out using GlPOx DM, a pronounced and much larger current increase was observed at all Glp concentrations and under all potential application conditions from 0.05V to 0.2V at all sampling times. The measurement of Glp concentrations lower than 0.5 mM was also possible. This was due to the fact that the mutations in GlPOx DM allow for electron transfer from the reduced FAD of GlPOx DM to the electron mediator Ru to be the dominant mode of electron transfer, which is preferable to electron transfer to oxygen. In addition, at all concentrations, the current was higher than those observed in the measurement using GlPOx WT.

Additionally, enzyme electrochemical sensing of D/L-glycerol-3-phosphate (Glp) was investigated using either wild type *A.viridans* GlPOx (GlPOx WT) or GlPOx Met104Phe/Asp169Glu (double mutant; DM) using interdigitated electrode (IDE) as the electrode. The experimental procedures are shown in FIG. 13. In all conditions, 0.005 U/µl of either GlPOxWT or GlPOxDM was used. For the substrate several concentrations of Glp were used together with electron mediator, Hexaammine ruthenium(III) chloride (CAS #14282-91-8), (Ru), and chronoamperometric measurements were carried out by applying potential; 0.05V, 0.1V or 0.2V versus counter electrode, and current was monitored at 1 sec, 5 sec, 10 sec and 30 sec after potential application (sampling time). The observed currents are plotted against Glp concentration to see Glp-dependent catalytic current. The results are shown in FIG. 14. When the enzyme electrochemical sensing of Glp was carried out using GlPOx WT, observed current increased with increased Glp concentration for all sampling times. However, the measurement of Glp concentrations lower than 0.2 mM was not possible. This was due to the fact that electron transfer from reduced FAD of GlPOx WT to the oxygen was the dominant mode of electron transfer, which is less preferable to electron mediator, Ru. In addition, at all concentrations, the current was lower than 0.3 µA, and therefore it was difficult to monitor Glp concentration using GlpOx WT as the enzyme. In contrast, when the enzyme electrochemical sensing of Glp was carried out using GlPOx DM, a pronounced and much larger current increase was observed in all Glp concentrations and under all potential application conditions from 0.05V to 0.2V in all sampling time. The measurement of Glp concentrations lower than 0.2 mM was also possible. This was due to the fact that the mutations in GlPOx DM allows for electron transfer from the reduced FAD of GlPOx DM to the electron mediator Ru to be the dominant mode of electron transfer which is preferable to electron transfer to oxygen. In addition, at all concentrations, the current was higher than those observed in the measurement using GlPOx WT.

Example 4: Saturation Mutagenesis Investigation of M104 and D169 Residues

Saturation mutagenesis (in which a protein residue is substituted with all possible amino acids at that position, and the wild-type protein is compared to the 19 mutants) was performed at the M104 and D169 positions of a glycerol 3-phosphate oxidase having SEQ ID NO: 1, and the dehydrogenase and oxidase activities of the resulting mutants were tested. The activities are shown in more detail in FIGS. 15 and 16.

Specifically, FIG. 15 (A) shows dehydrogenase activity (blue bar, left side of each pair) and oxidase activity (orange bar, right side of each pair) of the wild type glycerol 3-phosphate oxidase and 19 mutants at the M104 position. substituted each amino acid shown in horizontal axis for M104. Substitutions which resulted in increased dehydrogenase activity included M104V, M104F, M104A, M104P, M104Y, and M104G.

FIG. 15 (B) shows the percentage ratio of dehydrogenase activity against oxidase activity (Dh/Ox value) of wild type glycerol 3-phosphate oxidase and 19 mutants at the M104 position. Substitutions which resulted in an increased Dh/Ox value, compared to the wild-type, included M104V, M104F, M104P, M104N, M104I, and M104H. Since no oxidase activity was detected for M104R/D/K, their Dh/Ox values were not calculated.

FIG. 16 (A) shows dehydrogenase activity (blue bar, left side of each pair) and oxidase activity (orange bar, right side of each pair) of the wild type glycerol 3-phosphate oxidase and 19 mutants at the D169 position. substituted each amino acid shown in horizontal axis for M104. The D169E mutation resulted in increased dehydrogenase activity.

FIG. 16 (B) shows the percentage ratio of dehydrogenase activity against oxidase activity (Dh/Ox value) of wild type glycerol 3-phosphate oxidase and 19 mutants at the D169 position The D169E mutation resulted in an increased Dh/Ox ratio, compared to the wild-type.

Many modifications and other embodiments of the subject matter set forth herein will come to mind to one skilled in the art to which the subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A glycerol 3-phosphate oxidase mutant comprising a sequence having at least 95% sequence identity to SEQ ID NO: 1, with reduced oxidase activity as compared to the glycerol 3-phosphate oxidase of SEQ ID NO: 1 or increased dehydrogenase activity compared to the glycerol 3-phosphate oxidase of SEQ ID NO: 1, or both reduced oxidase and increased dehydrogenase activity compared to the glycerol 3-phosphate oxidase of SEQ ID NO: 1; and wherein said glycerol 3-phosphate oxidase mutant comprises a modification at one or more amino acid positions selected from:

(a) a position corresponding to position 104 of the amino acid sequence set forth in SEQ ID NO: 1, wherein the modification comprises a substitution of the amino acid residue Met with an amino acid residue selected from the group consisting of Ala, Asn, Gly, His, Ile, Phe, Pro, Tyr, and Val; and (b) a position corresponding to position 169 of the amino acid sequence set forth in SEQ ID NO: 1, wherein the modification comprises a substitution of the amino acid residue Asp with the amino acid residue Glu.

2. The glycerol 3-phosphate oxidase mutant of claim 1, comprising a sequence having at least 99% sequence identity to SEQ ID NO: 1.

3. The glycerol 3-phosphate oxidase mutant of claim 1, comprising a modification at one or more amino acid positions selected from:

(a) a position corresponding to position 104 of the amino acid sequence set forth in SEQ ID NO: 1, wherein the modification comprises a substitution of the amino acid residue Met with an amino acid residue selected from Phe and Val; and (b) a position corresponding to position 169 of the amino acid sequence set forth in SEQ ID NO: 1, wherein the modification comprises a substitution of the amino acid residue Asp with the amino acid residue Glu.

4. The glycerol 3-phosphate oxidase mutant of claim 1, having a reduced oxidase activity as compared to the glycerol 3-phosphate oxidase of SEQ ID NO: 1.

5. The glycerol 3-phosphate oxidase mutant of claim 1, having an increased dehydrogenase activity compared to the glycerol 3-phosphate oxidase of SEQ ID NO: 1.

6. The glycerol 3-phosphate oxidase mutant of claim 1, having an oxidase activity of 30% or less of that of the glycerol 3-phosphate oxidase of SEQ ID NO: 1, and a dehydrogenase activity of 50% or more of the glycerol 3-phosphate oxidase of SEQ ID NO: 1.

7. The glycerol 3-phosphate oxidase mutant of claim 1, comprising a modification at a position corresponding to position 104 of the amino acid sequence set forth in SEQ ID NO: 1, wherein the modification comprises a substitution of the amino acid residue Met with an amino acid residue selected from Phe, Pro, and Val.

8. The glycerol 3-phosphate oxidase mutant of claim 1, comprising a modification at a position corresponding to position 104 of the amino acid sequence set forth in SEQ ID NO: 1, wherein the modification comprises a substitution of the amino acid residue Met with an amino acid residue selected from Phe and Val.

9. The glycerol 3-phosphate oxidase mutant of claim 1, comprising a modification at a position corresponding to position 169 of the amino acid sequence set forth in SEQ ID NO: 1, wherein the modification comprises a substitution of the amino acid residue Asp with the amino acid residue Glu.

10. The glycerol 3-phosphate oxidase mutant of claim 1, modified at (a) a position corresponding to position 104 of the amino acid sequence set forth in SEQ ID NO: 1, wherein the modification comprises a substitution of the amino acid residue Met with the amino acid residue Phe; and (b) a position corresponding to position 169 of the amino acid sequence set forth in SEQ ID NO: 1, wherein the modification comprises a substitution of the amino acid residue Asp with the amino acid residue Glu.

11. A device for assaying triglyceride in a sample, the device comprising the glycerol 3-phosphate oxidase mutant of claim 1; and an electron mediator.

12. A kit for assaying triglyceride in a sample, the kit comprising the glycerol 3-phosphate oxidase mutant of claim 1; and an electron mediator.

13. An enzyme electrode comprising the glycerol 3-phosphate oxidase mutant of claim 1 immobilized on the electrode.

14. A method of assaying triglyceride in a sample, the method comprising the steps of: contacting the sample with the glycerol 3-phosphate oxidase mutant of claim 1; and measuring an amount of oxidized glycerol 3-phosphate.

15. The method of claim 14, wherein the glycerol 3-phosphate measured is L-glycerol 3-phosphate.

* * * * *

SEQUENCE LISTING

```
<160> NUMBER OF SEQ ID NOS: 1

<210> SEQ ID NO 1
<211> LENGTH: 611
<212> TYPE: PRT
<213> ORGANISM: Aerococcus viridans

<400> SEQUENCE: 1

Met Ser Lys Leu Ser Phe Lys Tyr Arg Lys Glu Thr Val Glu Gln Leu
1               5                   10                  15
```

```
Lys Glu Asn Gln Tyr Asp Leu Phe Ile Ile Gly Gly Ile Thr Gly
                20                  25                  30
Ala Gly Val Ala Ile Gln Ala Ala Ser Gly Leu Lys Thr Ala Leu
         35                  40                  45
Val Asp Met Gln Asp Phe Ser Glu Gly Thr Ser Ser Arg Ser Thr Lys
     50                  55                  60
Leu Val His Gly Gly Ile Arg Tyr Leu Lys Asn Phe Asp Leu Glu Val
65                  70                  75                  80
Val Ser Asp Thr Val Thr Glu Arg Ala Thr Val His Asn Ile Ala Pro
                 85                  90                  95
His Ile Pro Gln Pro Asp Pro Met Leu Met Pro Leu Tyr Asp Glu Pro
             100                 105                 110
Lys Val Thr Phe Asn Pro Leu Arg Leu Gln Ile Ala Met Asp Ile Tyr
             115                 120                 125
Asp Ser Leu Ala Gly Val Lys Asp Ser Gln Tyr Ala Asn Glu Met Leu
    130                 135                 140
Ser Lys Asp Glu Val Leu Ser Arg Gln Pro Asp Leu Met Ala Glu Gly
145                 150                 155                 160
Leu Ile Gly Gly Gly Lys Tyr Leu Asp Phe Asn Asn Asn Asp Ser Arg
                165                 170                 175
Leu Val Ile Glu Asn Ile Lys Gln Ala Asn Asp Asp Gly Ala Asp Leu
            180                 185                 190
Leu Ser His Ala Lys Val Val Gly Phe Glu Tyr Glu Asn Asp Lys Ile
        195                 200                 205
Val Ala Val Lys Val Glu Asp Leu Leu Ser Gly Glu Thr Phe Thr Val
    210                 215                 220
Lys Ser His Val Val Ile Asn Thr Thr Gly Pro Trp Ser Asp Thr Ile
225                 230                 235                 240
Arg Gln Leu Asp Gly Ser Asp Lys Lys Pro Ala Gln Met Arg Pro Thr
                245                 250                 255
Lys Gly Val His Phe Val Val Asp Lys Ser Lys Leu Thr Val Ser Gln
            260                 265                 270
Pro Ile Tyr Phe Asp Thr Gly Glu Gln Asp Gly Arg Met Val Phe Val
        275                 280                 285
Leu Pro Arg Glu Asn Lys Thr Tyr Phe Gly Thr Thr Asp Thr Asp Tyr
    290                 295                 300
Thr Gly Asp Phe Glu His Pro Thr Val Thr Gln Glu Asp Val Asp Tyr
305                 310                 315                 320
Leu Leu Arg Val Val Asn His Arg Phe Pro Asn Ala Asn Leu Ser Ile
                325                 330                 335
Asn Asp Ile Glu Ala Ser Trp Ala Gly Leu Arg Pro Leu Ile Asp Ser
            340                 345                 350
Asn Asn Ala Ser Asp Tyr Asn Gly Gly Asp Ala Gly Arg Leu Ser Glu
        355                 360                 365
Arg Thr Phe Asp Glu Leu Val Ala Leu Phe Asp Tyr Ser Lys Asp
    370                 375                 380
Lys Val Glu Arg Ser Thr Val Glu Asp Lys Leu Gln Asp Leu Gly Ser
385                 390                 395                 400
Asn Thr Ser Glu Arg Gly Asp Gly Ser Pro Ser Val Ser Arg Gly
                405                 410                 415
Ser Asp Leu Ser Val Ala Pro Ser Gly Leu Phe Thr Leu Ala Gly Gly
            420                 425                 430
Lys Ile Thr Asp Tyr Arg Lys Met Ala Lys Gly Ala Met Glu Arg Ile
```

```
                        435                 440                 445
Ile Pro Val Val Thr Asp Ile Thr Gly Lys Ser Tyr Glu Leu Val Gln
    450                 455                 460

Ser Ser Thr Tyr Pro Ile Ser Gly Gly Gln Phe Asp Pro Asn Ser Tyr
465                 470                 475                 480

Glu Thr Ala Met Glu Lys Phe Ala Asn Val Gly Val Ala Arg Gly Leu
                485                 490                 495

Thr Tyr Gly Gln Ser Leu Asn Leu Ala Lys Leu Tyr Gly Ser Asn Met
            500                 505                 510

Asn Arg Val Ile Ser Tyr Leu Pro Val Ala Lys Glu Tyr Ala Ala Lys
                515                 520                 525

Tyr Asp Tyr Pro Val Asp Ile Ala Val Ser Leu Ile Tyr Ala Leu Glu
            530                 535                 540

Glu Glu Gly Val Tyr Thr Pro Leu Asp Phe Phe Ala Arg Arg Thr Thr
545                 550                 555                 560

Phe Met Leu Phe Gln His Asp Lys Met Leu Ala Val Lys Glu Ala Val
                565                 570                 575

Ser Gln Thr Ile Val Asp Tyr Phe Gly Leu Asp Gln Ala Thr Ala Asp
            580                 585                 590

Gln Gln Lys Thr Ala Leu Asp Glu Glu Ile Ala Lys Ala Glu Leu Gln
        595                 600                 605

Tyr Leu Lys
    610
```